(12) United States Patent
Becker

(10) Patent No.: US 8,834,421 B2
(45) Date of Patent: Sep. 16, 2014

(54) RETROBULBAR SYRINGE INCLUDING SOFT CANNULA DISTAL END

(76) Inventor: Bruce Becker, Encino, CA (US)

( * ) Notice: Subject to any disclaimer, the term of this patent is extended or adjusted under 35 U.S.C. 154(b) by 0 days.

(21) Appl. No.: 13/283,695

(22) Filed: Oct. 28, 2011

(65) Prior Publication Data

US 2012/0041369 A1 Feb. 16, 2012

Related U.S. Application Data

(62) Division of application No. 12/496,431, filed on Jul. 1, 2009.

(60) Provisional application No. 61/077,294, filed on Jul. 1, 2008, provisional application No. 61/153,446, filed on Feb. 18, 2009.

(51) Int. Cl.
| | |
|---|---|
| A61M 5/178 | (2006.01) |
| A61M 5/32 | (2006.01) |
| A61M 5/315 | (2006.01) |
| A61F 9/00 | (2006.01) |
| A61F 9/007 | (2006.01) |

(52) U.S. Cl.
CPC ............. *A61M 5/329* (2013.01); *A61M 5/3291* (2013.01); *A61M 5/3286* (2013.01); *A61M 5/31511* (2013.01); *A61M 5/3243* (2013.01); *A61F 9/0017* (2013.01); *A61F 9/007* (2013.01); *A61M 5/3257* (2013.01)
USPC ........................ 604/164.01; 604/187; 604/195

(58) Field of Classification Search
USPC ............. 604/164.01, 164.02, 164.06, 164.12, 604/165.02, 166.01, 187, 194, 195, 604/506–508, 525
See application file for complete search history.

(56) References Cited

U.S. PATENT DOCUMENTS

| | | | |
|---|---|---|---|
| 3,989,044 A | | 11/1976 | Meierhoefer |
| 5,098,389 A | | 3/1992 | Cappucci |
| 5,201,718 A | | 4/1993 | Whisson |
| 6,193,695 B1 | | 2/2001 | Rippstein, Jr. |
| 6,206,856 B1 | | 3/2001 | Mahurkar |
| 6,413,245 B1 | | 7/2002 | Yaacobi et al. |
| 2002/0123723 A1 | | 9/2002 | Sorenson et al. |
| 2004/0116864 A1 | | 6/2004 | Boudreaux |
| 2005/0027256 A1 | * | 2/2005 | Barker et al. ............ 604/164.12 |
| 2007/0156094 A1 | | 7/2007 | Safabash et al. |
| 2008/0097397 A1 | * | 4/2008 | Vrba .............................. 604/525 |
| 2010/0010468 A1 | | 1/2010 | Becker |
| 2010/0119609 A1 | | 5/2010 | Dobak |

OTHER PUBLICATIONS

International Search Report and Written Opinion of the International Searching Authority for PCT Patent App. No. PCT/US2009/049435 (Aug. 26, 2009).
Final Office Action issued in co-pending U.S. Appl. No. 12/496,431 (Aug. 2, 2012).
Non-Final Office Action issue in co-pending U.S. Appl. No. 12/496,431 (Dec. 1, 2011).

\* cited by examiner

*Primary Examiner* — Kami A Bosworth
(74) *Attorney, Agent, or Firm* — Cermak Nakajima McGowan LLP; Adam J. Cermak

(57) ABSTRACT

A syringe and needle assembly includes a needle that extends through the barrel of the syringe and is attached to a proximal portion of the syringe. The distal end of the needle extends through a sleeve attached to the distal end of the syringe. The proximal end of the needle includes a spring which biases the needle proximally, so that the distal tip of the needle is normally retracted within the sleeve. The assembly can be used for injections in portions of a patient's body including delicate tissues that could be damaged if contacted by the needle tip.

11 Claims, 24 Drawing Sheets

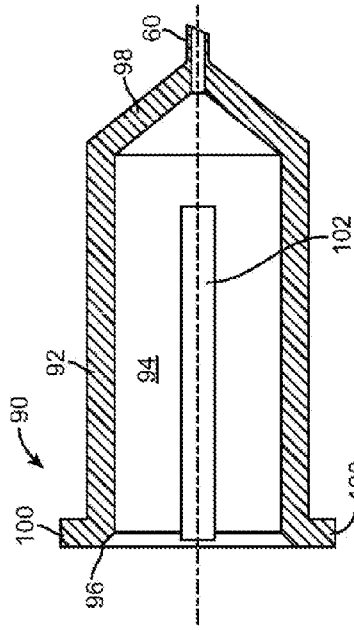
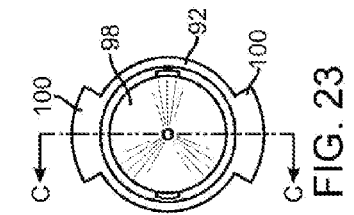
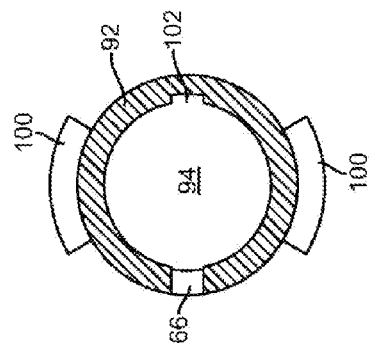
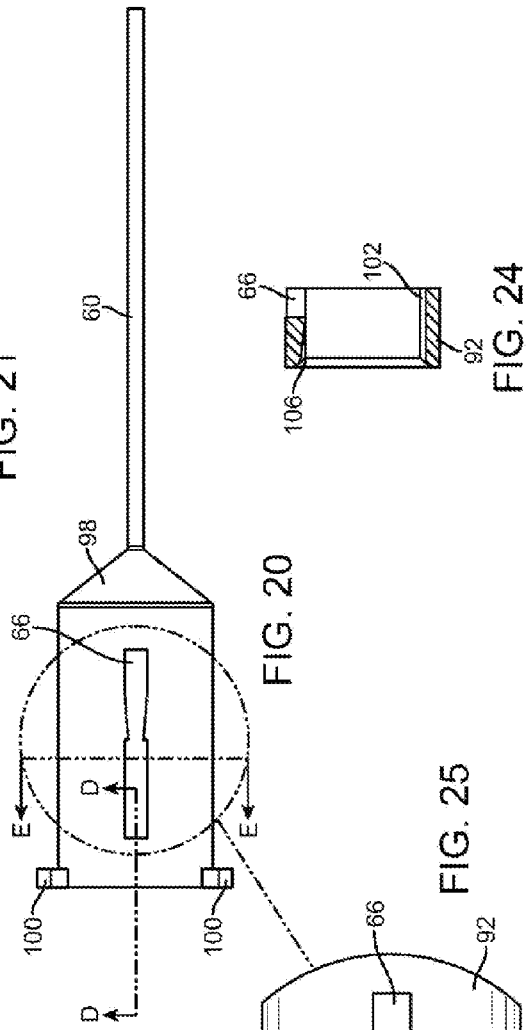
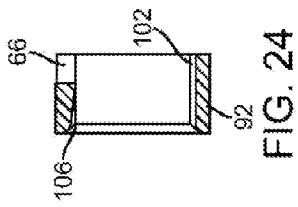
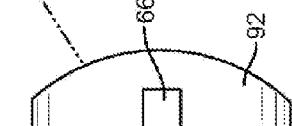
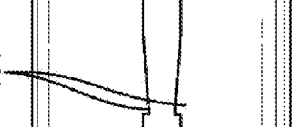
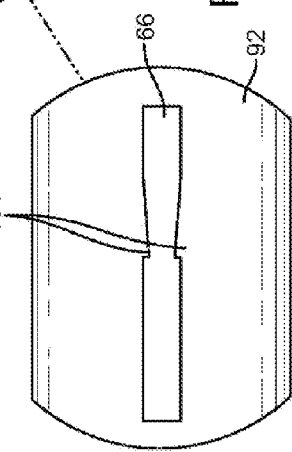

RETROBULBAR SYRINGE INCLUDING SOFT CANNULA DISTAL END

This application is a Divisional of, and claims priority under 35 U.S.C. §120 to, U.S. patent application Ser. No. 12/496,431, filed 1 Jul. 2009, which claimed priority under 35 U.S.C. §119 to U.S. Provisional patent application Nos. 61/077,294, filed 1 Jul. 2008, entitled "Retrobulbar Needle and Method of Use", and 61/153,446, filed 18 Feb. 2009, entitled "Retrobulbar Needle and Method of Use", the entireties of which are incorporated by reference herein.

BACKGROUND

1. Field of Endeavor

The present invention relates to devices, systems, and processes useful as needles and injectors, and more specifically to retrobulbar needles.

2. Brief Description of the Related Art

Many ophthalmology procedures are performed with a local anesthetic and intravenous sedation. Retrobulbar or peribulbar (behind the eye or adjacent to the eye) injections of local anesthetic are often used for intraocular surgeries, such as cataract extraction, retinal, vitreous, corneal, and pterygium surgeries. Retrobulbar injections are typically performed by placing a 1½ or 1¼ inch needle through the lateral lower lid adjacent to the inferior orbital rim and pushing deep into the orbit. In some cases the needle may be directed superomedially when it is deep in the orbit. This movement is to permit better flow of local anesthetic into the orbital apex. The local anesthetic is injected after the needle is in place. The needle is then withdrawn. The purpose of the local anesthetic is to provide anesthesia and akinesia (prevent movements of the eye which is critical during delicate intraocular surgery).

Peribulbar injections of local anesthetic involve placing the needle through the lateral lower lid adjacent to inferior orbital rim. However, the needle is not pushed as deep into the orbit as with a retrobulbar injection.

During these procedures, the surgeon cannot visualize the needle or orbital structures with this technique; that is, the needle is placed blindly. Therefore, vital structures such as the optic nerve, blood vessels, extraocular muscles, and the eye cannot be avoided.

Many complications can occur during retrobulbar, and to a lesser extent peribulbar, injections of local anesthetic. A retrobulbar hemorrhage can occur if the needle encounters a blood vessel. A severe retrobulbar hemorrhage can place pressure on the optic nerve and cause blindness. The needle can also puncture the eye which may result in severe visual loss. The needle can also penetrate the optic nerve sheath. The injection of a commonly used anesthetic, bupivicaine, causes respiratory arrest in these cases. An injection into an extraocular muscle can cause double vision.

An effort to avoid these complications has been the use of anesthetic eyedrops alone for cataract extractions. This technique is not possible in patients who are not cooperative and are too anxious. The use of anesthetic eyedrops alone is not possible for long surgeries such as retinal or vitreous surgeries. Retrobulbar anesthesia is still needed for patients who are anxious, unable to cooperate, or for retinal or vitreous surgeries, or corneal transplants.

An effort to reduce the complications of retrobulbar anesthetic injections is shown with the metal Atkinson retrobulbar needle. This needle is somewhat more rounded at the tip than typical needles used for local anesthetic injections. However, the needle is still sharp and metallic and can cause all of the complications listed above.

Another problem is that the injection is out the distal end of the needle only. The surgeon must angle the needle toward the optic nerve to make the anesthetic flow toward the orbital apex. This maneuver increases the rate of complications described above.

Greenbaum (U.S. Pat. No. 5,407,441, "Ophthalmologic cannula") describes an ophthalmologic cannula that has a blunt end. The blunt flexible cannula made of plastic is introduced into the orbit for a retrobulbar injection. The plastic is semi-flexible, but not soft. The cannula therefore still has the potential to tear a blood vessel or nerve. Furthermore, the surgeon must make an incision in the skin, muscle, and septum of the eyelid with scissors in order to allow the cannula to enter the orbit. The cannula has not been used because of the necessity of making an incision.

Longren et al (U.S. Pat. No. 4,886,506, "Soft tip catheter") describes a more rigid catheter with a softer section over the very distal portion of the catheter. It is used for coronary angiography to provide better torque control, but has a soft tip to avoid injury to the tissues. It is not a needle. Additional procedures and devices are needed to get the cannula into the blood vessel.

Razi (U.S. Pat. No. 5,542,936, "Sheath for introducing catheter") describes an introducer sheath for introducing a catheter into a blood vessel. There are fenestrations in the bend of the sheath for the flow of blood. This device has four separate pieces.

Gupta (U.S. Pat. No. 5,718,693, "Hematoma prevention apparatus and method") describes a needle which is placed in a blood vessel, a guidewire is placed through the needle into the vessel, and the needle is withdrawn. A cannula is then introduced over the guidewire. A sheath is then placed over the cannula such that part of the sheath is in the blood vessel and part is outside the skin. This prevents blood from leaking out of the blood vessel and causing a hematoma. This device uses four separate pieces.

Del Cerro et al (U.S. Pat. No. 5,273,530, "Intraretinal delivery and withdrawal instruments" and U.S. Pat. No. 5,409,457, "Intraretinal delivery and withdrawal instruments") describe a curved needle which has a very short sharp segment on the end. It is placed beneath the conjunctiva close to the eye and then pushed through the sclera posteriorly into the eye in the subretinal space. The sharp tip of the needle is always exposed. The needle does not go through the eyelid. The sharp needle tip is not covered at any time.

Erskine (U.S. Pat. No. 5,795,339 "Catheter-advancement actuated needle retraction system") describes a needle for intravenous use whereby the needle retracts inside an outer sheath after the needle has entered the vein. A spring mechanism is used. The mechanism allows the needle to be thrown away after its use with the sharp end retracted to avoid an inadvertent of a needle stick injury to the physician or nurse. The retactor mechanism is not used to protect structures in the patient.

Sorenson et al (U.S. Patent Application Publication No. 2002/0123723 A1, "Apparatus and method for specific interstitial or subcutaneous diffusion and dispersion of medication") describes a tube in which a sharp-pointed stylette is placed. The stylette allows the tube with the stylette to be pushed through a lining into the body for treatment. The stylette is removed and the tube can be pushed safely further into the body. Medication can then be injected through the tube into the body. Holes in the sidewall of the tube permit dispersion of the medication. The durometer of the material can be variable. This device involves two separate pieces.

Vaillancourt (U.S. Pat. No. 4,655,750, "Closed system catheter with guide wire") describes a needle with a sheath over it. The needle and sheath are introduced into a vein. The needle is withdrawn and a guidewire is pushed through the sheath into the vein. The sheath is pushed in further and the guidewire is withdrawn. This system has three separate pieces and does not protect the tissues when the needle is in place.

Couston et al (U.S. Patent Application Publication No. 2006/0149194, "Ophthalmic microsurgical system") describes an outer blunt cannula that can be flexible. The cannula is placed in the eye through a surgical incision. The end of the cannula is placed close to Schlemm's canal inside the eye. Various instruments can be passed through the cannula (e.g., knife, needle, etc.) to perform procedures on Schlemm's canal without injuring other intraocular structures. The instrument is never placed in the orbit. The procedure is performed under direct visualization.

Rogers (U.S. Pat. No. 5,531,692, "Safety syringe") with a plunger mechanism. There is an outer sheath over the needle. When the plunger is pushed, the needle tip sticks out the sheath. The needle tip retracts inside the sheath when there is no pressure on the plunger. The needle is used to prevent accidental needle-sticks in medical personnel.

Needles are also used during other types of surgery for the injection of local anesthetic. In many procedures, the same syringe and needle are used repeatedly. That is because the local anesthetic effect may dissipate during the procedure, or the surgery may extend to more areas that were not anesthetized by the original injections. In other cases, areas of bleeding require additional injections to allow the epinephrine in the local anesthetic to constrict the blood vessels and stop the bleeding.

The same needle and syringe are used repeatedly because of the added time (and cost) to obtain a new needle for each of many injections. The cap must be placed on the needle between uses. The needle and syringe must be picked up, placed on a tray, handed from the surgical technician to the surgeon and vice versa, and otherwise handled. All of these maneuvers place the operating personnel at a risk for an accidental needle stick and the transmission of disease such as HIV and hepatitis C.

There are various safety needles for injections and the placement of intravenous lines available. However, all of these needles and intravenous needles/lines are for a single use only.

SUMMARY

A first of many aspects of the present invention includes a syringe comprising a cylindrical barrel having a proximal end, a distal end, an interior wall, and an open interior space between the proximal and distal ends, a plunger assembly including a plunger stem having a proximal end and a distal end, and a piston attached to the plunger stem distal end, the piston forming a fluid seal with the barrel interior wall, a cannula attached to the barrel, the cannula including a longitudinally extending lumen, a proximal portion, and a distal portion having a flexibility greater than the cannula proximal portion; and a needle assembly including a longitudinally extending shaft having a proximal end, a distal end, and a lumen extending proximally from the needle shaft distal end, at least one side hole formed along the needle shaft, and a proximal body mounted to the needle shaft proximal end, the proximal body sealing the proximal end of the needle shaft lumen, the proximal body positioned proximal of the piston.

Another aspect includes an assembly comprising a hollow cylinder having an open proximal end and a distal end, a needle hub attached to the cylinder adjacent to the cylinder distal end, the needle hub including a proximal end, a distal end, and a hollow interior, an elongate needle having a proximal end, a sharpened distal end, and a lumen extending between the needle proximal and distal ends, the needle mounted to the needle hub with the needle lumen in communication with the needle hub interior, an elongate outer member having a proximal end, a distal end, and at least two laterally spaced arms longitudinally extending outside of the hollow cylinder, a cannula hub attached to the elongate outer member distal end, the cannula hub including a proximal end, a distal end, and a hollow interior, an elongate cannula having a proximal end, a blunt distal end, and a lumen extending between the cannula proximal and distal ends, the cannula mounted to the cannula hub with the cannula lumen in communication with the cannula hub interior, wherein the elongate needle is partially positioned in the cannula lumen, wherein the needle hub is partially positioned in the cannula hub, and wherein the hollow cylinder, needle hub, and needle are longitudinally movable relative to the elongate outer member, the cannula hub, and the cannula between a first position at which the needle distal end is distal of the cannula distal end, and a second position at which the needle distal end is proximal of the cannula distal end.

Yet another aspect includes a method of performing an injection into an anatomical location of a patient, the method comprising providing a needle and a cannula, the cannula having a distal end, the needle having a sharpened distal end, the needle positioned and longitudinally movable within the cannula between a distal position at which the needle sharpened distal end is distal of the cannula distal end, and a proximal position at which the needle sharpened distal end is proximal of the cannula distal end, moving the needle into the distal position, inserting the needle and the cannula into the anatomical location, moving the needle into the proximal position, and injecting a fluid through the distal end of the cannula.

Still other aspects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to exemplary embodiments of the apparatus and method, given only by way of example, and with reference to the accompanying drawings, in which:

FIG. 20 illustrates a top plan view of other portions of the embodiment of FIG. 11;

FIG. 21 illustrates a longitudinal cross-sectional view of the portions of FIG. 20;

FIG. 22 illustrates a lateral cross-sectional view taken at line C-C in FIG. 23;

FIG. 23 illustrates a proximal end view of the portions of FIG. 20;

FIG. 24 illustrates a longitudinal cross-sectional view taken at line D-D in FIG. 20;

FIG. 25 illustrates an enlarged view of the encircled portion of FIG. 20;

DETAILED DESCRIPTION OF EXEMPLARY EMBODIMENTS

Figure 1:
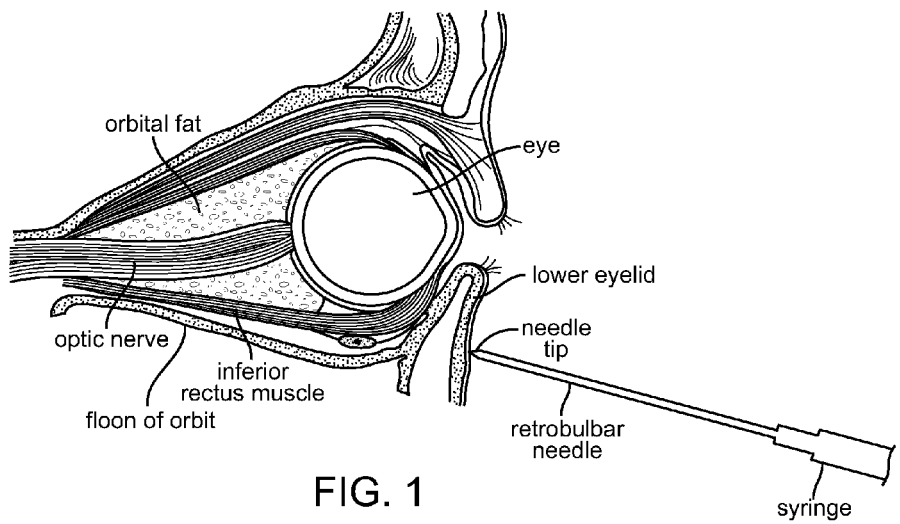
FIG. 1 illustrates a vertical cross-sectional view of the anatomy of the human orbit and adjacent structures, during a first stage of a retrobulbar injection.

Referring to the drawing figures, like reference numerals designate identical or corresponding elements throughout the several figures. Throughout this application, the term "distal" refers to the needle point end of the device, while the term "proximal" is at the end closer to the handle of the device and to the practitioner who manipulates the device.

In general terms, devices and processes embodying principles of the present invention involve unique and novel methods and devices to safely administer local anesthetics in areas of the body prone to complications from the injection of local anesthetics, including:

for retrobulbar and peribulbar anesthetic injections;

for anesthetic injections in other regions where injury to local structures can occur, such as lumbar punctures (spinal needles), aspiration of pleural effusions, and injections of the chest wall with local anesthetic; and for surgeries and procedures in any area of the body where there are repeated injections to protect medical personnel from accidental needle sticks.

In further general terms, a retrobulbar needle allows retrobulbar injections of the orbit without the risk of puncture of the delicate eye, optic nerve, and other fragile structures. An exemplary device embodying principles of the present invention includes an inner hub and metal needle, and an outer hub with a sheath on its distal end that covers the needle. The sheath is composed of a firm nonmetallic material except for the very distal end which is softer. A cover barrel covers the assembly prior to use. An outer hub plunger is attached to the outer hub and extends over the syringe. The needle is screwed onto a standard syringe and then the cover barrel is removed prior to use. The metal needle tip is exposed during the early needle placement. This includes the placement of the needle through the very lateral inferior lower lid which includes skin and muscle, and then the orbital septum just into the orbit. The physician then pushes on the outer hub plunger. This pushes and locks the sheath over the metal needle tip. The metal needle tip is then entirely contained within the firm portion of the sheath and the very distal soft end of the sheath. The needle can then be pushed deeper into the orbit, because the orbital fat has no resistance. The end of the sheath is soft and therefore will not penetrate the eye, optic nerve, or other delicate structures. The anesthetic is injected and flows out the end of the needle and also a hole in the sidewall of the metal needle and sheath.

A similar needle can be used for lumbar punctures (now done with spinal needles), thoracentesis, injection of anesthetic in the chest wall, and any area of the body covered with skin and muscle or other tough tissue but has soft fragile structures within.

With general reference to others of the several drawing figures, numerous aspects of devices and methods embodying principles of the invention will be described. Another exemplary retrobulbar needle assembly has a metal needle with a sharp rounded point. The proximal end of the metal needle is encased in a plastic hub (an "inner hub"). The inner hub is constructed such that it can be screwed into a syringe. The inner hub can have a length of 23 mm, although other sizes can be used. The distal portion (e.g., 2 mm) of the hub is tapered down to fit over the proximal end of the needle. The metal needle has an opening in its sidewall close to the opening in the distal end. This allows local anesthetic to flow forward and out the sidewall and thus flow to more than one desired anatomic area during the injection and reduce the need to change the angle of the needle during the injection. The outside diameter of the inner hub is 6 mm and the inside diameter is 4 mm; other sizes can be used.

An outer hub with a long external sheath connected to the distal end of the outer hub is provided that fits snugly over the inner hub and the metal needle. The sheath has a small hole in its sidewall close to the distal end. When the retrobulbar needle assembly is screwed into position, the hole in the walls of the sheath and metal needle are in the same longitudinal axis. A mark on the outer hub is in the same longitudinal axis as the small holes in the walls of the sheath and needle. The mark enables the physician to determine the location of the holes after the needle is inside the lid and orbit. The sheath is connected to the outer hub which fits over the inner hub. The outer hub has an extension which projects at a right angle from the hub and then extends in a direction proximal to the hub and fits over the attached syringe. The proximal end of the extension stops short of the syringe handle. The proximal end of the extension includes a ring that fits snugly around the syringe. This extension is called the "outer hub plunger."

The inner hub has a, e.g., 5 mm elevated lock segment that runs along the longitudinal axis. This segment has a design that allows it to lock the outer hub in its final position when the outer hub is pushed distally into position. The outer hub has a, e.g., 10 mm opening that runs along the longitudinal axis and is over the elevated lock segment of the inner hub.

The inner hub has a flange on its very proximal end that is screwed into the syringe. This flange is, e.g., 1 mm thick and, e.g., 8 mm in length and of a suitable width. The inner hub has a second flange that is, e.g., 5 mm from its proximal end and is, e.g., 11 mm in diameter and, e.g., 1 mm thick. The second flange has two slots 180 degrees apart. The slots are, e.g., 2 mm wide and, e.g., 0.5 mm deep. The slots allow a cover barrel to be fixated to the inner hub.

The outer hub has two elevated pieces 180 degrees apart that are, e.g., 1 mm from the proximal end of the external hub. The elevated pieces are, e.g., 0.5 mm in thickness and, e.g., 1 mm high. Each elevated piece extends around the circumference 60 degrees. The hub plunger attaches to the two elevated pieces on the outer hub.

The outer hub fits over the inner hub such that the distal end of the sheath is just proximal to the sharp end of the metal needle. This position is maintained during the "early phase" of needle placement.

A very short segment of the distal most end of the sheath is a softer (lower durometer) material than the proximal sheath. This is accomplished by using wire coil or braid for the proximal end of the sheath and ending the wire coil or braid just distal to the end of the sheath. Alternatively, a softer material can be used for the very distal end of the sheath. The softer material may be attached to the proximal sheath by interdigitating or other methods. Another method is to modify the material during processing and formation of the sheath such that the distal end is softer than the proximal sheath, such as by blending polymers of different hardnesses.

An exemplary procedure involves filling a standard syringe (e.g., a 10 cc syringe) with local anesthetic by placing a standard needle on the end of the assembly and suctioning the anesthetic into the syringe by pulling the plunger toward the proximal end of the syringe. The filling needle is removed and the safety needle assembly with both inner and outer hubs, and cover barrel in place is screwed into the distal end of the syringe. The cover barrel is pulled off when the needle and syringe are ready for use. The physician then pushes the safety needle assembly into the lateral lower lid adjacent to the inferior orbital rim. The needle is pushed through the skin and muscle and orbital septum just into the orbit (early phase of needle placement). The skin and, to a lesser degree the muscle and orbital septum, are the only tissues that are resistant to penetration. The orbit is filled with fat that offers little resistance and can be easily penetrated by a blunt instrument.

The physician then pushes on the outer hub plunger. This pushes the outer hub and thus the sheath distal to the end of the metal needle point. The distal soft segment of the sheath and a short segment of the proximal firm sheath are distal to the metal needle point. Thus, only the softer and blunt end of the sheath is in contact with the tissues, not the sharp metal point of the core needle. The metal needle point is entirely contained in the tougher (higher durometer) portion of the sheath. The very distal softer segment of the sheath starts just distal to the point of the needle.

Therefore, the metal needle point will never come into contact with the orbital tissues. The locking mechanism on the inner and outer hubs locks them into their final positions, i.e., with the metal needle point covered. This locks the sheath into its new position or "protection position." The needle assembly is then pushed deeper into the orbit. The soft and blunt end of the sheath easily slides through the orbital fat and does not have the risk of penetrating the eye, optic nerve, or blood vessels, or extraocular muscles.

The two small holes in the distal sidewalls of the metal needle and the sheath are aligned, preferably exactly, after the sheath is pushed into the protected position. The mark on the proximal outer hub allows the surgeon to orient the holes in the direction of the orbital apex (i.e., medially). The local anesthetic will therefore flow toward the orbital apex and straight forward, thus delivering the anesthetic to the desired locations without having to move the end of the needle toward the apex, a maneuver which would increase the possibility of contacting the eye, optic nerve, or blood vessels.

The method and device can be used in other areas of high risk, such as the injection of the chest wall, in a lumbar puncture, during a thoracentesis, and in any "fragile" area covered by skin or muscle or other lining.

Figure 2:
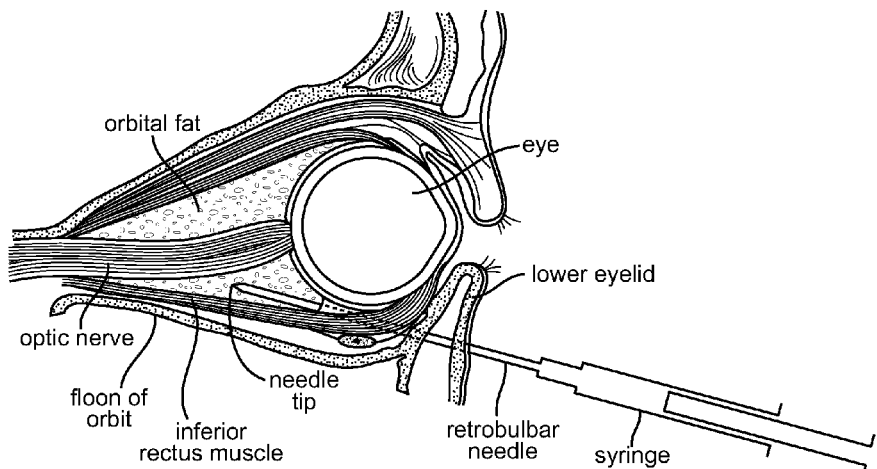
FIG. 2 illustrates a vertical cross-sectional view of the anatomy of the human orbit and adjacent structures, during a second stage of a retrobulbar injection.

FIG. 1 illustrates a cross-sectional view of the eye of the human patient. As illustrated in the drawing figure, the eye is bounded by the lower eyelid and inferior rectus muscle and orbital fat. The optic nerve extends posteriorly from the eye and the floor of the orbit is also illustrated. In prior methods, a retrobulbar needle attached to a syringe was inserted through the lower eyelid and into the orbital fat, as illustrated in FIG. 2.

Figure 3:
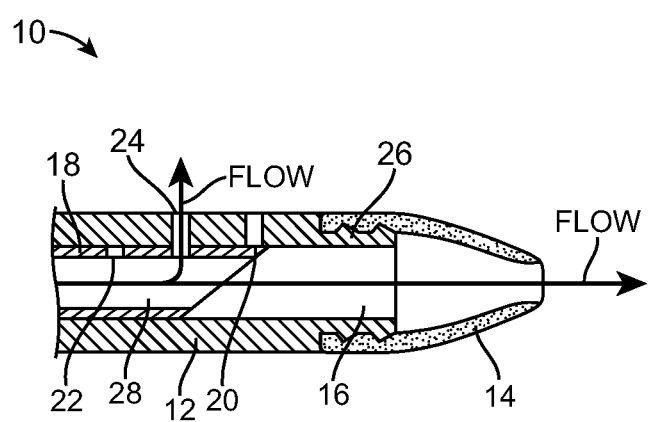
FIG. 3 illustrates an enlarged longitudinal cross-section view of the distal tip of a first exemplary embodiment of a needle and cannula in accordance with the present invention.

FIG. 3 illustrates the distal in portions of an exemplary cannula embodying principles of the president mentioned. The cannula 10 includes an outer sheath 12 which may be formed of a polymer, e.g., Pebax, or another rigid material and a softer material or softer segment of the same material 14 attached to the distal end of the outer sheath. The outer sheath 12 includes a longitudinally extending lumen 16. A needle 18 extends through the lumen 16, and is preferably sized so that there is a small, or no, gap between the outer surface of the needle in the inner surface of the outer sheath 12. The needle 18 includes a longitudinally extending lumen 28 and a sharp tip 20 at the distal end of the needle. Advantageously, the distal end of the outer sheath 12 can be attached to the resilient tip 14 by any known method; and the exemplary embodiment illustrated in FIG. 3, the outer sheath 12 includes a swag tip 26. As described in greater detail elsewhere herein, it is advantageous when the needle 18 in the outer sheath 12 include lateral holes 22, 24 which can be aligned so that the flow of fluid from the needle can exit through both the lateral holes and the distal end of the cannula 10.

Figure 4:
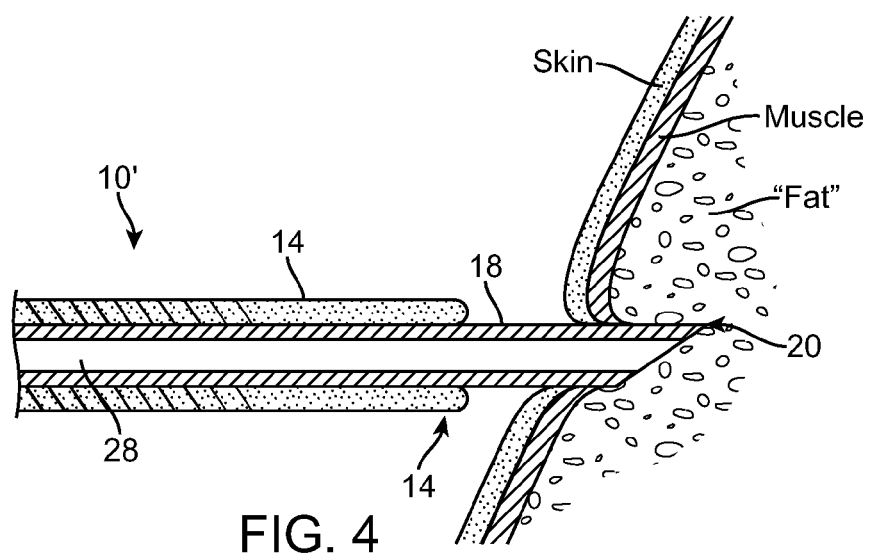
FIGS. 4 and 5 illustrate exemplary steps in a retrobulbar injection.
Figure 5:
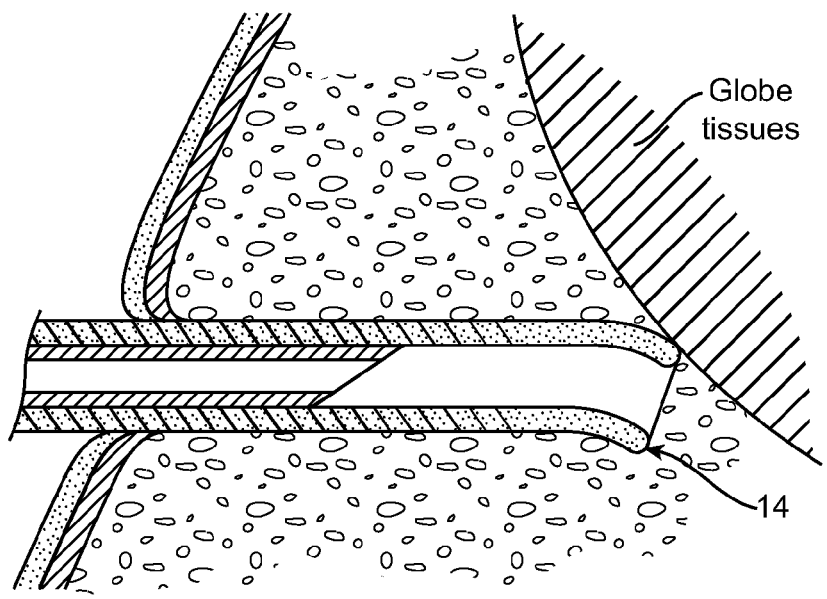

FIG. 4 illustrates in general terms an exemplary use in accordance with principles of the present invention. A cannula 10' is inserted through the skin of the patient with the sharp tip 20 of the needle 18. The needle tip 20 extends through the skin and underlying muscle and into the fat of the orbit adjacent to the eye. As illustrated in FIG. 5, the outer sheath is extended over the needle and through the fat surrounding the eye. Because the outer sheath includes a soft tip, it can come into contact with the orbital tissues without risking damage to the same.

Figure 6:
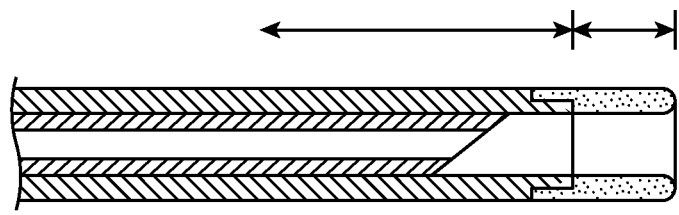
FIGS. 6-10 illustrate additional exemplary embodiments of cannulae in accordance with the present invention.
Figure 7:
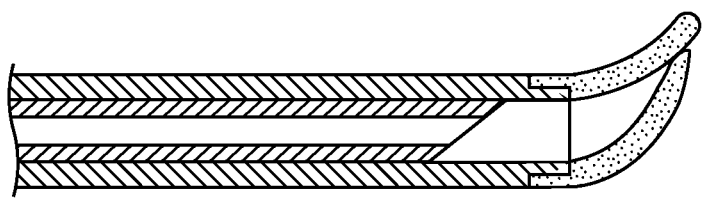
Figure 8:
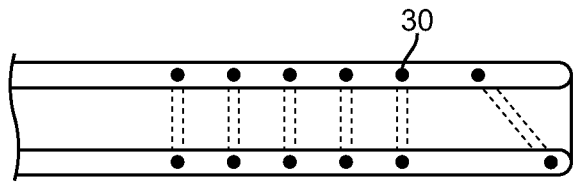
Figure 9:
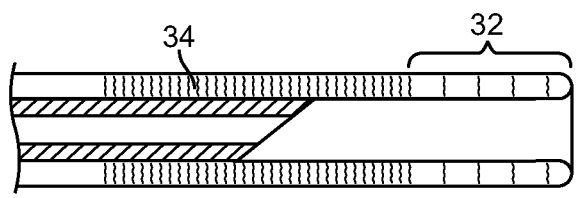
Figure 10:
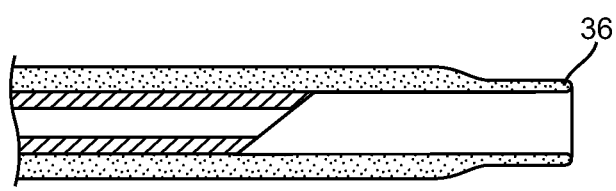

FIGS. 6 through 10 illustrate several additional embodiments of an outer cannula embodying principles of the present invention. In the embodiment of FIG. 6, a different softer material which is more flexible than the proximal portions of the cannula, is used for the distal tip. FIG. 7 illustrates the relative flexibility of the material of the tip of the embodiment of FIG. 6, for example when the distal tip of the cannula comes into contact with the eye of the patient. In the embodiment of FIG. 8, a reinforcing spring 30 may be used which is embedded in the cannula material and which is wound more widely in the distal and so that the distal end of the cannula is more flexible. In the embodiment illustrated in FIG. 9, the outer cannula includes a less dense material 32 at the distal end of the cannula, with a more dense material 34 used in the proximal portions of the cannula. In the embodiment illustrated in FIG. 10, the distal end of the cannula includes a portion 36 with a reduced diameter, so that the distal end of the cannula is again more flexible. Furthermore, combinations of the several embodiments described here it can be used together to form an outer cannula with a flexible distal tip.

Figure 11:
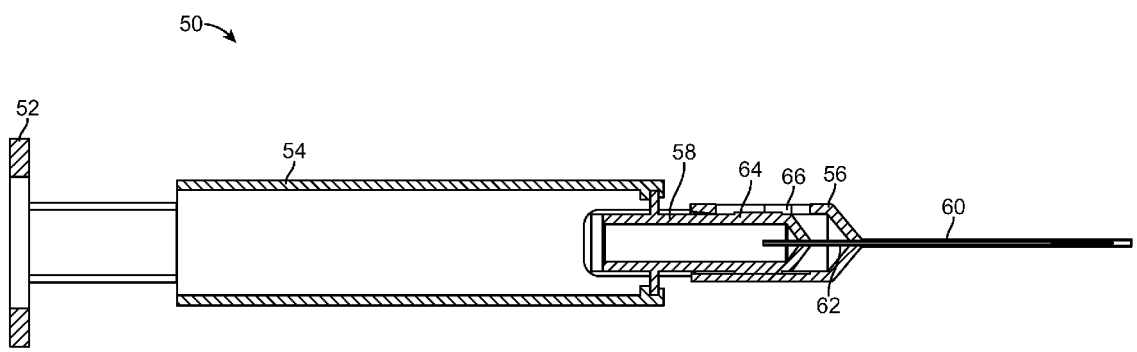
FIG. 11 illustrates a longitudinal cross-sectional view of an exemplary embodiment of a needle assembly in accordance with the present invention.
Figure 12:
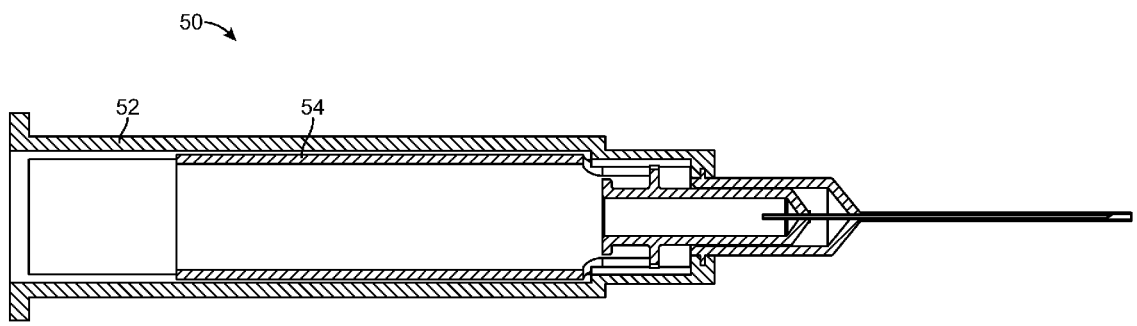
FIG. 12 illustrates a longitudinal cross-sectional view of the exemplary embodiment of FIG. 11, taken in a plane rotated ninety degrees relative to the plane of the view of FIG. 11

FIGS. 11 and 12 illustrate an exemplary embodiment of a retrobulbar needle embodying principles of the present invention. The retrobulbar needle 50 includes an outer hub plunger 52 and an inner hub holder 54. The outer hub plunger is attached to an outer hub 56, and the inner hub holder is attached to an inner hub 58. A sheath 60 extends distally for the distal end of the outer hub 56, while a needle 62 extends from the distal end of the inner hub 58. A locking flange 64 extends laterally from the outer surface of the inner hub 58 into a slot 66 formed in the outer hub 56. FIG. 12 illustrates the same embodiment 50 illustrated in FIG. 11, but taken in a longitudinal plane that is rotated 90 degrees relative to the section of view of FIG. 11. Thus, it can be seen that the outer hub plunger 52 only partially surrounds the inner hub holder 54. It can also be seen that be the inner hub holder 54 includes a space in its interior which is sized and configured to receive the barrel of a syringe in it, and so that proximal portions of the inner hub 58 mates with distal portions of the standard syringe in a known manner.

Figure 13:
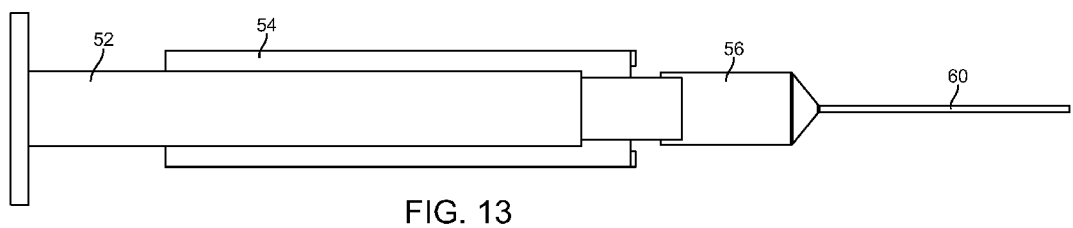
FIG. 13 illustrates a top plan view of the embodiment illustrated in FIG. 11, taken in the same direction.
Figure 14:
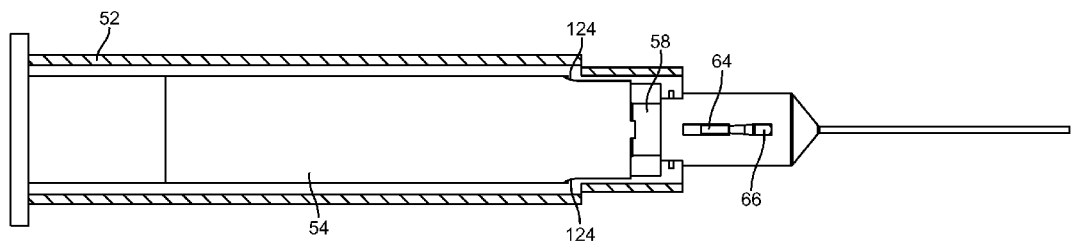
FIG. 14 illustrates a partial longitudinal cross-sectional view, and a partial side elevational view, taken in the same direction as FIG. 12.
Figure 18:
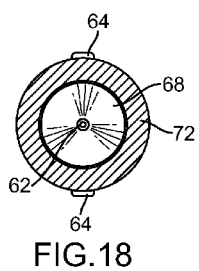
FIG. 18 illustrates a lateral cross-sectional view taken at line B-B in FIG. 16.
Figure 17:
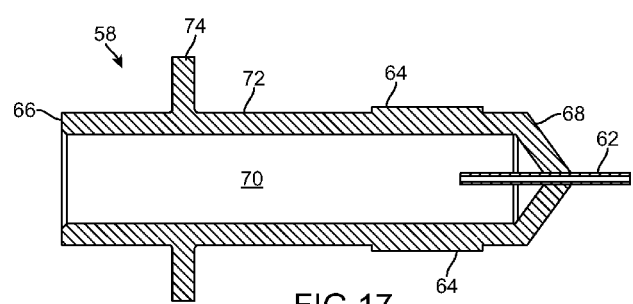
FIG. 17 illustrates a longitudinal cross-sectional view, taken at line A-A in FIG. 19.

FIG. 13 illustrates a side elevational view of the needle 50 of FIGS. 11 and 12, and plainly shows that the outer hub plunger 52 only partially surrounds the inner hub holder 54, while still connecting with the outer hub 56. FIG. 14, shows a partial cross-sectional view and shows the outer hub plunger engaging the outer hub 56, also illustrates how the inner hub holder engages with the inner hub, and how the flanges 64 and slot 66 in the inner and outer hubs, respectively, are engaged.

Figure 15:
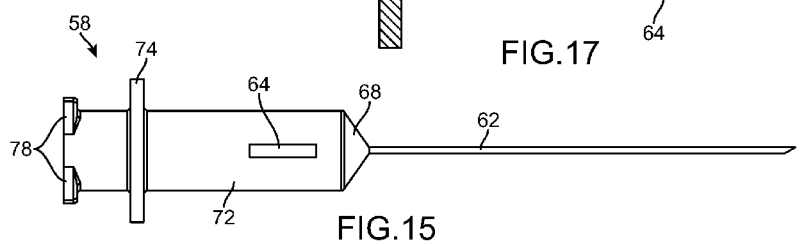
FIG. 15 illustrates a top plan view of a portion of the embodiment of FIG. 11.
Figure 19:
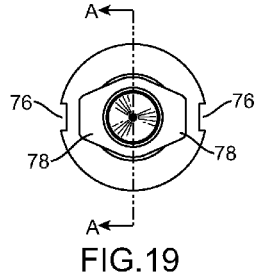
FIG. 19 illustrates a proximal end view of the portion of FIGS. 15 and 16.
Figure 16:
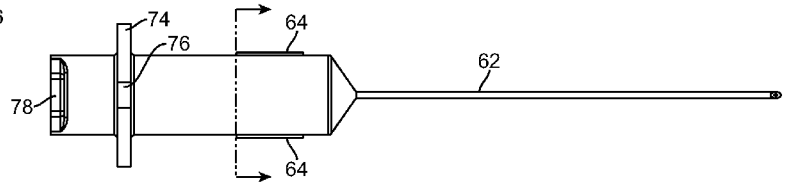
FIG. 16 illustrates a front side elevational view of the portion of FIG. 15.

FIGS. 15 through 19 illustrate several views of the inner hub 58. With reference to FIG. 15, the inner hub 58 includes a generally cylindrical body 72 from which extends a circumferential flange 74. The inner hub 58 includes a blind bore 70 which extends from an open proximal end 66 to a closed tapered distal end 68. As can be seen in each of the drawing figures, the locking flange 64 preferably includes two laterally extending flanges 64, one of which cooperates with the slot 66 in the outer hub as described elsewhere herein. The needle 62 extends through the tapered distal end 68 such that the interior lumen of the needle is in fluid communication with the interior bore 70. As can be seen in FIGS. 15, 16, and 19, the proximal end of the inner hub 58 includes at least one, and preferably several, standard lugs 78 which are configured to mate with the standard interior screw threads of a syringe, as would be readily understood by those of ordinary skill in the art. As can be readily seen in FIGS. 16 and 19, the circumferential flange 74 includes a pair of notches 76, which are preferably circumferentially spaced 180 degrees.

FIGS. 20 through 25 illustrate numerous views of the outer hub 90. The outer hub 90 includes a generally cylindrical body 92 including an open proximal end 96 and a closed and tapered distal end 98. The cannula 60 extends distally from the distal end 98, and is in communication with a blind bore 94. The outer hub 90 includes a pair of laterally and partially circumferentially extending flanges 100 positioned at the proximal end of the outer hub. As can be best seen in FIGS. 21 and 22, the interior surface of the cylindrical body 92 includes a slot 102 which extends only partially through the side wall of the hub, and which is diametrically opposed to the slot 66. The internal slot 102 is sized and positioned to receive one of the flanges 64 of the inner hub 58 to assist in aligning and guiding the movement of the inner hub relative to the outer hub. The proximal flanges 100 are provided to be engaged by distal portions of the outer hub plunger 52, as illustrated for example in FIGS. 12 and 14, while the circumferential flanges 74 of the inner hub are provided to be engaged by distal portions of the inner hub holder 54, as illustrated in FIGS. 11 and 13.

FIG. 24 illustrates an enlarged sectional view, take that line D-D of FIG. 20. As can be seen in FIG. 24, proximal portions of the cylindrical body 92 adjacent to the slot 66 includes a ramp portion 106, which is provided so that the flange 64 of the inner hub can more easily enter into the slot 66 when the inner hub and outer hub are assembled together. With reference to FIG. 25, the slot 66 includes at least one, and preferably a pair, of opposed ramps 104. The inwardly extending ramps 104 are provided as a one-way lock mechanism that cooperate with the locking flanges 64 of the inner hub to inhibit, and preferably prevent, the inner hub and outer hub from moving relative to each other when the flange 64 is in the proximal portions of the slot 66.

Figure 28:
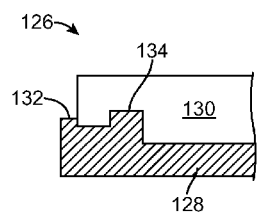
FIG. 28 illustrates a portion of a longitudinal cross-sectional view taken at line F-F in FIG. 27.
Figure 27:
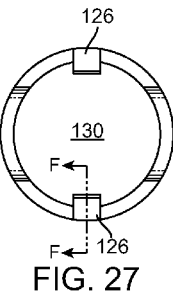
FIG. 27 illustrates a distal end view of the portions of FIG. 26.
Figure 26:
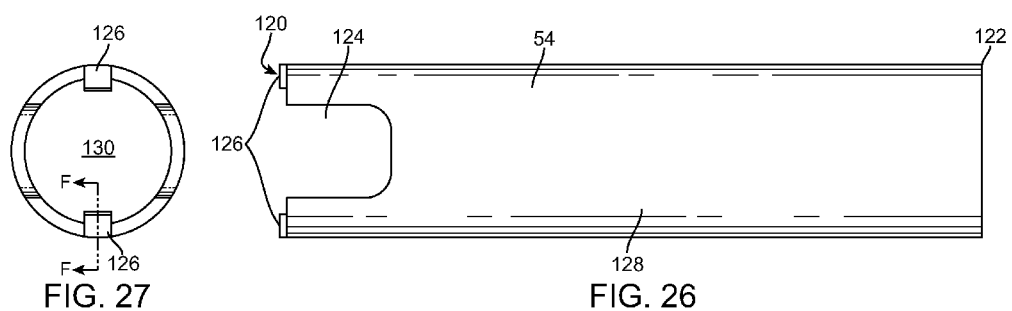
FIG. 26 illustrates a top plan view of yet further portions of the embodiment of FIG. 11.
Figure 30:
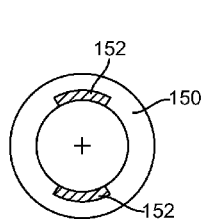
FIG. 30 illustrates a lateral cross-sectional view taken at line G-G in FIG. 29.

In FIGS. 26 through 28 are illustrated other portions of the inner hub holder 54. FIG. 26 illustrates a side elevational view of the inner hub holder, with the proximal end 122 and a distal end 120. The inner hub holder 54 advantageously includes a pair of windows or cutouts 124 from adjacent to the distal end 120, and which provide clearance between the inner hub holder 54 and the outer hub plunger and 56. The inner hub holder 54 is formed of a generally cylindrical body 128 and includes locks 126 formed at the distal end. FIG. 27 shows a side elevational view of the distal end of the inner hub holder 54, and illustrates the radially inwardly extending locks 126. The locks 126 are configured to receive and form a snap fit with the flange 74 of the inner hub.

FIG. 28 illustrates a cross-sectional view taken that line F-F of FIG. 27. The locks 126 include a first radial flange 132 and a larger second radial flange 134 which is the spaced proximally of the first radial flange, and together define a well between the flanges 132, 134 which is sized to receive the flange 74 of the inner hub. FIGS. 27 and 28 also illustrate the inner lumen 130 of the inner hub holder 54.

Figure 33:
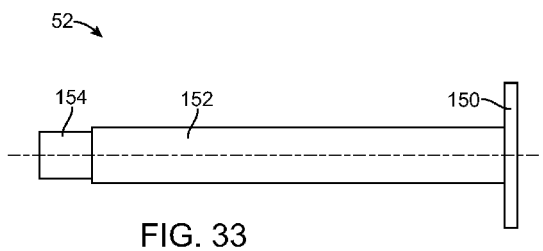
FIG. 33 illustrates a front side elevational view of the embodiment of FIG. 29, taken at a view rotated ninety degrees from the view of FIG. 29.
Figure 32:
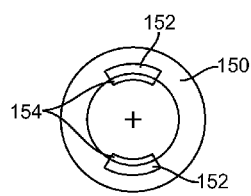
FIG. 32 illustrates a distal end view of the portions illustrated in FIG. 29.
Figure 29:
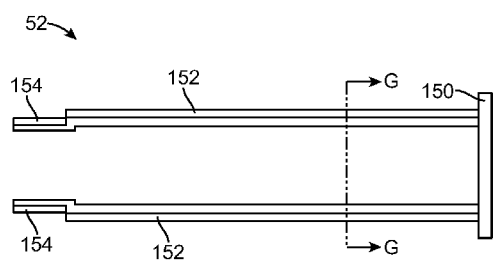
FIG. 29 illustrates a top plan view of further portions of the embodiment of FIG. 11.
Figure 31:
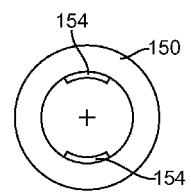
FIG. 31 illustrates a proximal end view of the portions illustrated in FIG. 29.

FIGS. 29 through 33 illustrate several views of the outer hub plunger 52. The outer hub plunger 52 includes at least one, and advantageously two or more, arms 152 which extend from a proximal flange 150 towards a number of distal fingers 154. As can be seen in the comparison of FIGS. 29 and 33, the arms 152 have a relatively small circumferential size, which gives the user of the device access to the inner hub holder 54, as described elsewhere herein. The distal fingers 154 are provided to lock or otherwise mount to the flange 100 of the outer hub 90. For purposes of simplicity, the distal ends of the distal fingers 154 are illustrated in a simplistic form and do not show the locking structures which connect the distal fingers to the outer hub 56.

Figure 34:
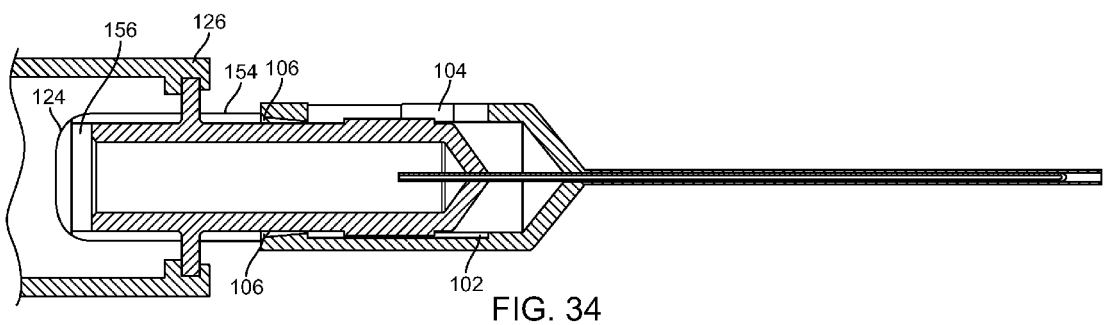
FIG. 34 illustrates an enlarged view of distal portions of the illustration of FIG. 11.
Figure 35:
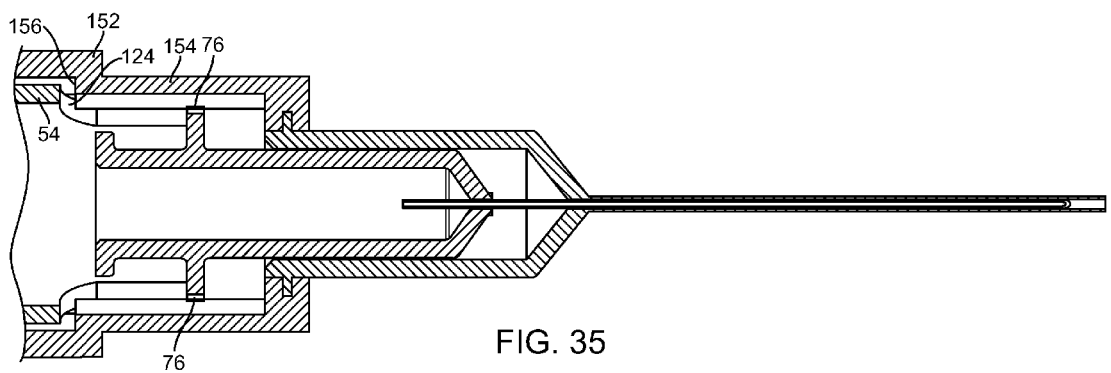
FIG. 35 illustrates an enlarged view of distal portions of the illustration of FIG. 12.

FIGS. 34 and 35 are enlarged longitudinal sectional views which illustrate some of the features of the first embodiment from FIGS. 11 and 12. As can be seen in FIGS. 34 and 35, the windows 124 provide additional access to the inner hub, while the lock 126 engages the flange of the inner hub. In FIG. 34, the step or shoulder 156 between the arm 152 and the finger 154 can also be seen, as well as the finger 154 extending to the outer hub. Similarly, in FIG. 35, the window 124 of the inner hub holder 54 can be seen providing clearance between the inner hub holder and the outer hub plunger 52, especially at the shoulder 156. Also, the notches 76 in the flange 74 can be seen providing clearance for the fingers 154.

Use of the first exemplary embodiment 50 will be described with reference to FIGS. 11 and 12. A standard syringe, not illustrated, is attached to the inner hub 58 and the lugs 78 in a known matter. The inner hub 58 and outer hub 56 are positioned relative to each other as generally is illustrated in FIGS. 11 and 34, with the flange 64 extending into the slot 66. The inner hub holder 54 is pushed distally relative to the outer hub holder 52, which causes the sharpened distal end of the needle 62 to extend past the distal end of the sheath 60. In this configuration, the sharpened distal end of the needle 62 can be used to penetrate through tissues adjacent to the eye of the patient. Once the distal end of the needle has entered into the retrobulbar fat, the outer hub plunger 52 and the inner hub holder 54 are manipulated to retract the inner hub 58 and the needle 62 proximally relative to the outer hub 56 and the sheath 60, so that the sharpened distal end of the needle is retracted within the lumen of the sheath 60. In this protected orientation of the needle and sheath, the combination can be pushed further into the fatty tissues adjacent to the patient's eye without risking puncturing or otherwise damaging any of the delicate tissues of the eye. When the practitioner decides to inject fluid from the standard syringe through the cannula, the practitioner merely pushes on the plunger of the standard syringe, which is accessible through the proximal end of the outer hub plunger 52, which expresses fluid from the standard syringe through the inner hub 58 through the needle 62, into the distal most portions of the sheath 60 and out of the distalmost end of the sheath. Because the arms 152 of the outer hub plunger have a small circumferential size, the inner hub holder is readily accessible by the practitioner when the needle assembly 50 is in the assembled configuration, making it a simple matter to manipulate both the outer hub plunger 52 and the inner hub holder 54. When the practitioner has injected a sufficient amount of fluid from the standard syringe into the eye, the practitioner merely pulls the entire assembly proximally from the insertion site in the patient's eye.

Another exemplary retrobulbar needle allows retrobulbar injections of the orbit which reduces, or eliminates, the risk of puncture of the delicate eye, optic nerve, and other fragile structures. A syringe includes a sleeve attached to its distal end. The sleeve has a relatively long proximal higher durometer (firm) segment and a short distal relatively soft segment. A rigid, e.g., metal, needle extends from the sleeve through the center of the entire syringe. The syringe has a handle on its proximal end and a laterally extending strut over the proximal end of the syringe. The needle extends through the strut. The needle has a flat button on its proximal end. There is a spring on the needle between the button and the strut. The spring keeps the distal sharp tip of the metal needle inside the firm segment of the sleeve, that is, the spring biases the needle proximally. When the physician pushes on the button, the spring is compressed and the sharp distal tip of the needle is pushed outside the distal end of the sleeve. The needle can now be pushed through the very lateral inferior lower lid which includes the tougher skin and muscle, and then orbital septum just into the orbit. The physician then releases pressure on the button and the needle tip retracts into the firm proximal segment of the sleeve by the force of the spring. The sleeve with the soft end can now be pushed through the orbit, because the orbital fat has no resistance. The end of the sheath is soft and therefore will not penetrate the eye, optic nerve, or other delicate structures. The anesthetic is injected and flows out the end of the needle and also a hole in the sidewall of the needle and sheath.

A similar needle can be used for lumbar punctures (now done with spinal needles), thoracentesis, injection of anesthetic in the chest wall, and any area of the body covered with skin and muscle or other tough tissue but has soft fragile structures within.

A similar needle without the soft distal end can be used for injections of local anesthetic in any tissues. In this embodiment medical personnel are protected from needle sticks and the needle can be used repeatedly during the case.

Figure 36:
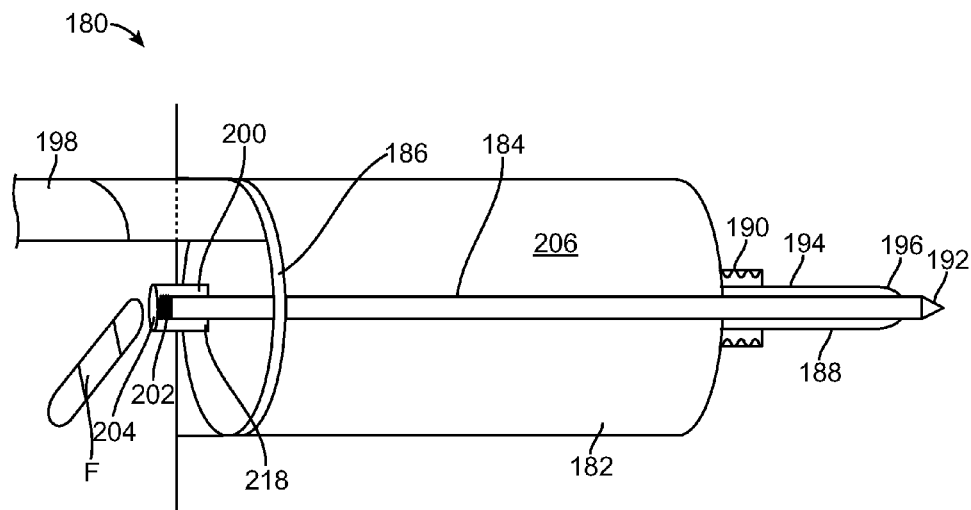
FIG. 36 illustrates, in a schematic manner, another embodiment of a needle assembly embodying principles of the present invention.

With reference to FIG. 36, which schematically illustrates a second exemplary embodiment, a needle assembly 180 has a generally cylindrical syringe barrel 182 and handle 198 made of typical materials and of standard sizes (e.g., 5 cc, 6 cc, 10 cc, etc) or other sizes. However, the projection of the distal end of the syringe includes a thin-walled sleeve 188, preferably formed of a polymeric material, that has a narrow diameter. The sleeve 188 has an internal diameter that is just large enough to fit over a (preferably metal) needle 184 of a desired diameter, which includes a sharp distal point 192. The proximal end of the needle 184 extends all the way to the proximal end of the syringe barrel 182. The proximal end of the needle has a flat button 204 that may be round or of another desired shape, and optionally can include a loop (not illustrated) attached to the button or to the proximal end of the needle 184. The button 204 and/or the loop is positioned and configured to be pushed by the physician during placement of the needle, e.g., with a finger F.

Figure 37:
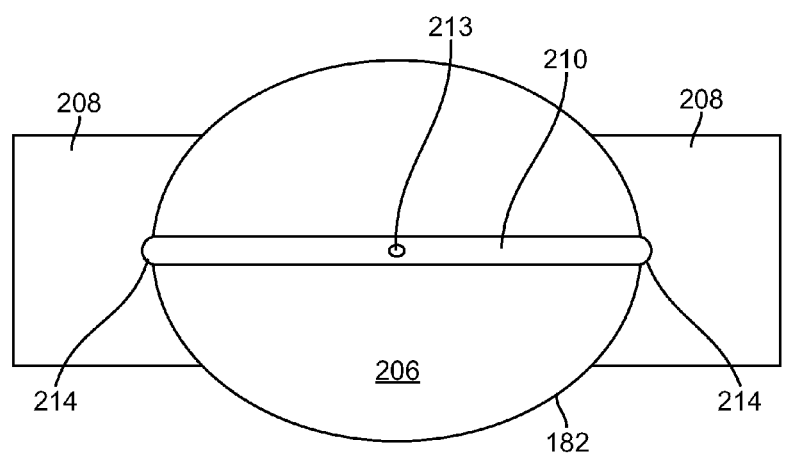
FIG. 37 illustrates a proximal end view of the embodiment of FIG. 36.
Figure 38:
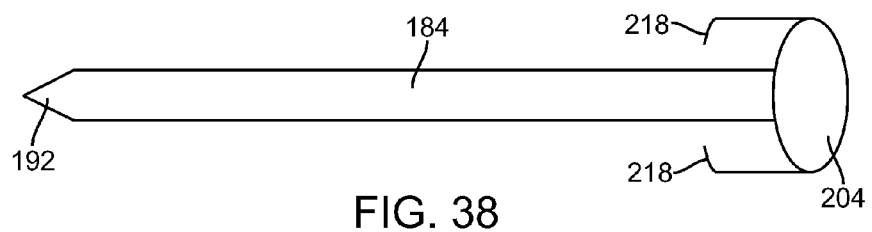
FIGS. 38 and 39 illustrate an exemplary needle and cover of the embodiment of FIG. 36.

A thin strut 210 extends across the proximal end of the syringe (see FIG. 37). The ends of the strut 210 each have a fixation piece 214 that is L-shaped. The fixation piece 214 allows the strut to be fixed on each end into small openings in the laterally extending syringe handle 208 during manufacturing. The strut 210 includes a hole 212 through the strut, through which the needle 184 extends. The needle 184 extends through the strut hole 212, through the distal portion of the plunger 186, through the lumen 206 of the syringe barrel 182, and out the distal end of the syringe barrel.

With reference to FIG. 36, the button 204 on the proximal end of the needle has a device 200 which permits the needle to slide a predetermined distance relative to the syringe; in the embodiment illustrated in FIG. 36, the device 200 includes L-shaped pieces 218 extending distally along each side of the needle 184 from the button 204. Each L-shaped piece 218 fits through small holes in the strut (not illustrated) adjacent to the hole 212. The L-shaped pieces 218 prevent the needle 184 from moving too far proximally and dislodging from the syringe. A spring 202 fits over the needle 184 between the button 204 and the strut 210. The spring 202, thus positioned between the button 204 and the proximal face of the syringe, causes the needle 184 to retract inside the sheath 194 when the physician is not pushing on the button.

Figure 41:
FIGS. 41 and 42 illustrate an exemplary plunger portion of the embodiment of FIGS. 36 and 40.
Figure 42:
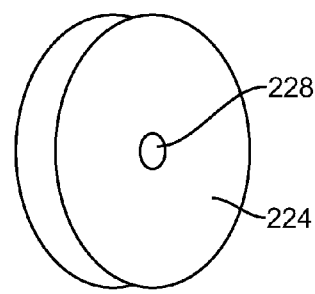

The plunger 186 has a typical distal end with a rubber cap 224 over its distal end that is similar to typical plungers. However, unlike typical plungers, the plunger and rubber cap have holes 226, 228, in their centers which are at most the diameter of the external diameter of the needle 184 to form a fluid seal. The proximal end of the plunger 222, seen in FIG. 41, has a flat, usually round surface. The physician can push of the flat proximal end 222 of the plunger to push it further into the syringe barrel 182. The stem 198 of the plunger is advantageously semicircular and extends from the flat proximal end 222 to the distal round end 186 of the plunger. The semicircle preferably extends 90 degrees, but may be more or less, thus permitting access to the space adjacent to the stem 198 and between the proximal and distal ends of the plunger from the side. The semicircular stem 198 has a diameter that is just slightly less than the internal diameter of the syringe barrel 182. The position of the semicircular stem allows room for the physician to put his/her digit (finger, thumb) on the button 204 of the needle and push on it to extend the sharp end 192 of the needle 184 beyond the distal end 196 of the sleeve 194.

Figure 40:
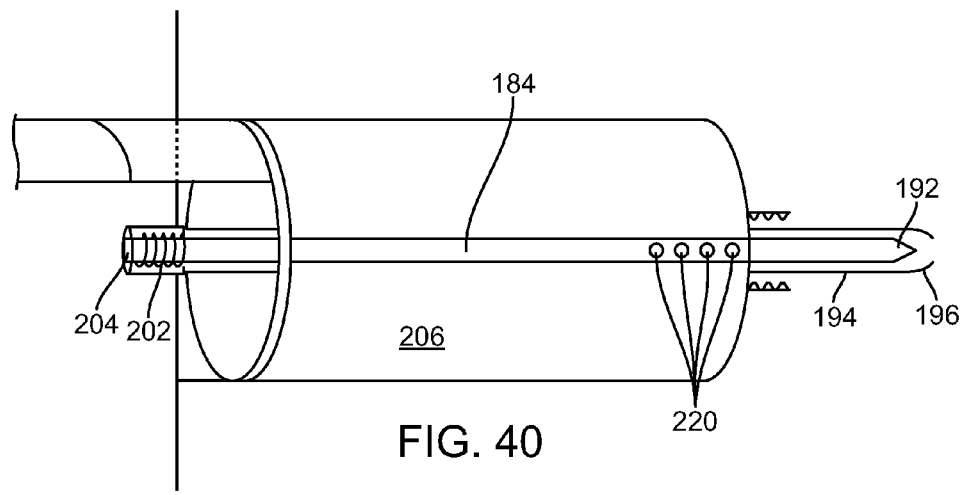
FIG. 40 illustrates a view similar to FIG. 36, with the needle retracted proximally.

The syringe barrel has a cylinder 190 extending from the syringe distal end (see FIGS. 36 and 40). The cylinder 190 is of a larger diameter than the sleeve 22 and much shorter that the sleeve, and optionally includes internal threads which allow a separate, larger gauge needle (e.g., an "anesthetic aspirating needle", not illustrated) to be screwed into the cylinder 190. The larger aspiration needle, when used, extends over the sheath. The separate aspiration needle can be used to draw local anesthetic out of a local anesthetic container, usually a bottle or vial. The larger aspirating needle is then unscrewed from the cylinder 190 and removed after the local anesthetic is drawn into the syringe interior 206. Alternatively, a standard needle can be used; however, if a very large gauge needle is needed to slide over the sleeve, then in another embodiment, the distal portion of the needle (e.g., the distal 5 to 10 mm) is of smaller diameter, which insures that the hole made in the bottle of anesthetic is not too large.

Figure 39:
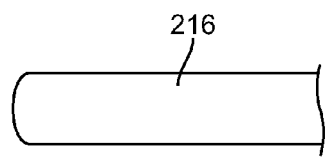

A cover is preferably provided for the separate larger anesthetic aspirating needle (the needle will already have a cover if a standard needle is used) and a separate cover 216 for the sheath of the syringe (FIG. 39).

When the syringe 180 is used for retrobulbar or peribulbar injections of local anesthetic, it has a short distal end 196 of the sleeve 188 that is relatively soft (see FIGS. 3 and 6-10). The longer, proximal portion 194 of the sleeve 188 is constructed of a stiffer material than the distal end; however, the proximal portion of the sleeve need not be as hard as metal. When the needle 184 is retracted proximally within the sleeve 188, the sharp end 192 of the needle 184 retracts into the more rigid proximal portion 194 of the sleeve.

The very short segment 196 of the distalmost end of the sleeve 188 is formed of a softer material than the proximal portion 194 of the sleeve, e.g., by forming the distal portion of a material with a lower durometer or other similar construction, such as those described elsewhere herein. Alternatively, the proximal, stiffer portion can be reinforced, while the distal portion can be less reinforced or not reinforced at all, which can be accomplished by using a wire coil or braid for the proximal end of the sheath and ending the wire coil or braid just distal to the end of the sleeve. Alternatively, a softer material can be used for the very distal end of the sleeve. The softer material may be attached to the proximal sleeve by interdigitating or other methods. Another embodiment includes modifying the material during processing and formation of the sleeve such that the distal end is softer than the proximal sleeve.

Figure 43:
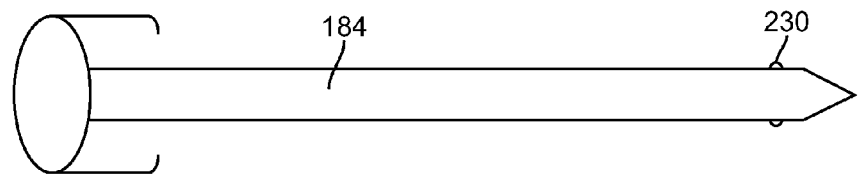
FIG. 43 illustrates another exemplary needle.

In another exemplary embodiment, illustrated in FIG. 43, a thin collar 230 is provided on the needle 184 just proximal to the sharp distal end 192. The collar 230 can prevent the soft distal end of the sleeve from being compressed when the sharp distal end of the needle is pushed through the skin and muscle. The collar can still be retracted inside the firmer portion of the sleeve when necessary.

Another advantageous use of a syringe embodying principles of the present invention is for protection of medical personnel. When the syringe is used for injections in areas other than the orbit or around the eye or into other spaces, such as adjacent to the lungs (i.e., a thoracentesis), then there optionally is no soft distal end of the sleeve. The firm sleeve protects the medical personnel from accidental needle injections. The sharp distal end of the needle is always within the sleeve unless the physician pushes on the button to cause the sharp distal end of the needle to extend outside the sleeve.

With reference to FIG. 40, the needle 184 includes flow holes 220 in the sidewalls of the needle that are close to the distal end of the syringe, but are contained within the cavity 206 of the syringe. The flow holes allow the flow of anesthetic between the needle and the syringe when the piston is pushed distally, which is necessary because the proximal end of the needle 184 is sealed.

The manufacture of the syringe can advantageously be performed with the following steps, although any order can be used a will be readily understood by those skilled in the art.
1. The plunger is placed into the syringe.
2. The strut is snapped into position with each end being snapped into the handle of the syringe.
3. The spring is placed onto the metal needle.
4. The metal needle and spring are pushed through from the proximal end of the syringe through the center of the plunger and into the sleeve.
5. The clips on the button of the metal needle are clipped through and onto the strut.

With reference to the several drawing figures, an exemplary process of using a syringe will now be described.

The larger gauge anesthetic aspirating needle with its cover (neither illustrated) is screwed into the larger diameter cylinder 190 with internal threads that extends from the distal end of the syringe. The cover is withdrawn from the aspirating needle and the aspirating needle is inserted into a bottle of anesthetic. The syringe plunger is pulled proximally to draw anesthetic into the syringe, flowing through the needle 184, through the holes 220, and into the interior 206 of the syringe barrel. The cover is then placed over the aspiration needle, and the cover and aspiration needle are unscrewed and removed from the syringe 180. The cover 216 for the sleeve 188 can now be placed over the sleeve, if desired.

The cover 216 is later removed from the sleeve 188 when it is desired to make an injection. The physician pushes on the button 204 to push the sharp end 192 of the needle 184 out of the distal end 196 of the sheath 188. The physician then pushes the needle 184 into the tissue or part of the body into which s/he desires to inject the anesthetic. S/he can release the pressure on the button 204 (usually the thumb is used to push in the button) when the needle penetrates into the desired anatomic location. In many areas of the body, the anatomy below the skin and muscle is softer than the skin. Thus, the sleeve 188 can be pushed through the deeper tissues without the use of the sharp needle tip 192. The physician then can inject anesthetic from the syringe barrel, through the holes 220, through the retracted end 192 of the needle, past the distal end 196 of the sleeve 188, and into the anatomical location of choice. The sleeve 188 is optionally removed at the completion of the injection. The syringe 180 can be safely handed to the other medical personnel without the risk of an accidental needle stick, because the tip 192 of the needle 184 is safely contained within the sheath 188.

For use of the syringe 180 for retrobulbar or peribulbar injections of local anesthetic, the cover 216 is removed from the sheath 188. The physician pushes on the button to push the sharp end 192 of the needle 184 out of the distal end of the sheath 188. The physician then pushes the needle through the skin of the inferotemporal eyelid, muscle, and orbital septum into the soft orbital fat. The skin and, to a lesser degree, the muscle of the eyelid and orbital septum, are the only tissues that offer resistance. The orbit is filled with fat that offers little resistance and can be easily penetrated by a blunt instrument, e.g, the sheath 188.

The physician then can release the pressure on the button (usually the thumb is used to push in the button) when the needle penetrates into the orbit. The needle 184 thus retracts into the tougher, e.g., higher durometer, proximal portion of the sleeve 188. The distal soft segment 196 of the sleeve 188 and a short segment of the proximal firm sleeve are distal to the needle point 192. Thus, only the softer blunt end 196 of the sleeve 188 is in contact with the tissues, and not the sharp point 192 of the needle 184, because the needle point 192 is entirely contained in the higher durometer portion of the sleeve. The very distal softer segment 196 of the sleeve 188 starts just distal to the point of the needle when the needle is in its retracted orientation relative to the sleeve.

The length of the device 200 is selected so that the distance that the needle can be moved proximally and distally relative to the syringe 180 and sleeve 188 is sufficient for the needle 184 to extend past the distal-most end of the sleeve 188, when in the needle's distal-most configuration, and so that the needle's tip 192 is within the stiffer portion 194 of the sleeve when in the needle's proximal-most configuration. Therefore, the needle point 192 will never come into contact with the orbital tissues when used in accordance with principles of the present invention. The needle assembly 180 is then pushed deeper into the orbit. The soft blunt end 196 of the sleeve 188 easily slides through the orbital fat and does not have the risk of penetrating the eye, optic nerve, or blood vessels.

In one embodiment, as described generally with respect to FIG. 3, at least two small holes are provided in the distal sidewalls of the needle 184 and the sleeve 188 which are exactly aligned (in those designs which have holes in the sidewalls) after the sleeve is pushed into the position protecting the needle tip 192. A mark (not illustrated) can be provided on the very proximal-most portion of the sleeve 188 which allows the surgeon to orient the holes in the direction of the orbital apex (i.e., medially). The local anesthetic will therefore flow toward the orbital apex in addition to straight forward, thus delivering the anesthetic to the desired locations without having to move the end of the needle toward the apex, a maneuver which would increase the possibility of contacting the eye, optic nerve, or blood vessels.

The syringe 180 is removed at the completion of the injection. The syringe can be safely handed to the other medical personnel without the risk of an accidental needle stick.

The devices described herein can also optionally be used for other areas of the anatomy of high risk for needle puncture of delicate structures. The methods and devices can be used in other areas of high risk, such as the injection of the chest wall, in a lumbar puncture, during a thoracentesis, and in any "fragile" area covered by skin or muscle or other lining.

For use for injection of local anesthetic during any procedure or area of the body, the metal needle tip will always be retracted into the firm sheath when not in use. The distal soft segment will not be needed in many areas of the body. This will protect medical personnel from accidental needle sticks while allowing the syringe and needle to be used multiple times.

Figure 44:
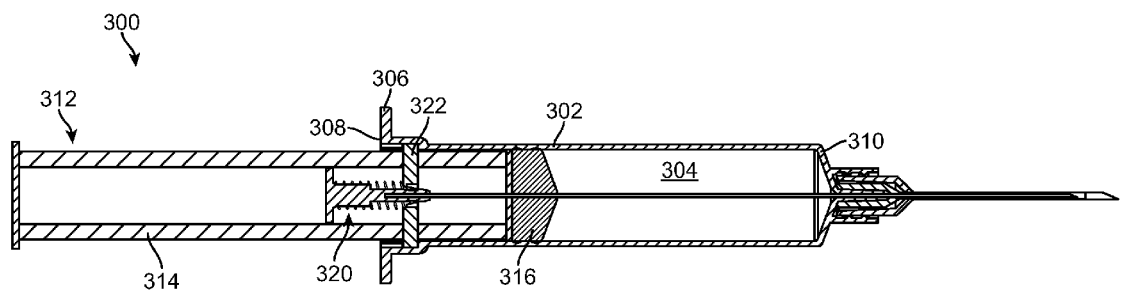
FIG. 44 illustrates a longitudinal cross-sectional view of yet another exemplary needle assembly embodying principles of the present invention.
Figure 45:
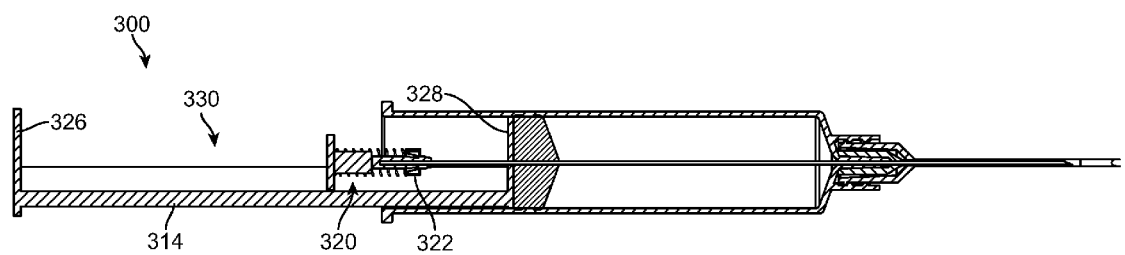
FIG. 45 illustrates a longitudinal cross-sectional view of the embodiment of FIG. 44, taken in a plane rotated ninety degrees from the plane of view of FIG. 44.

FIGS. 44 and 45 illustrate a third exemplary embodiment of a retrobulbar needle assembly 300 embodying principles of the present invention. The assembly 300 is similar in some respects to the assembly 180 described with reference to FIG. 36 above. The assembly 300 includes a cylindrical syringe barrel 302 having a hollow interior space 304, a proximal flange 306 defining a proximal opening 308, and a closed distal end 310. A plunger assembly 312 extends proximally from the barrel 302 and includes a plunger stem 314 and a distally mounted piston 316. A needle assembly 320 it is mounted to the syringe barrel 302 via a stabilizer bar 322. Extending distally from the closed the distal end 310 of the syringe barrel 302, the assembly 300 includes a cylindrical, internally threaded collar 324. As better seen in FIG. 45, the plunger stem 314 includes a proximal flange 326 and a distal flange 328 which together define an open space 330 which is large enough to permit a practitioner's digit, e.g., a thumb or finger, to access the proximal end of the needle assembly 320.

Figure 46:
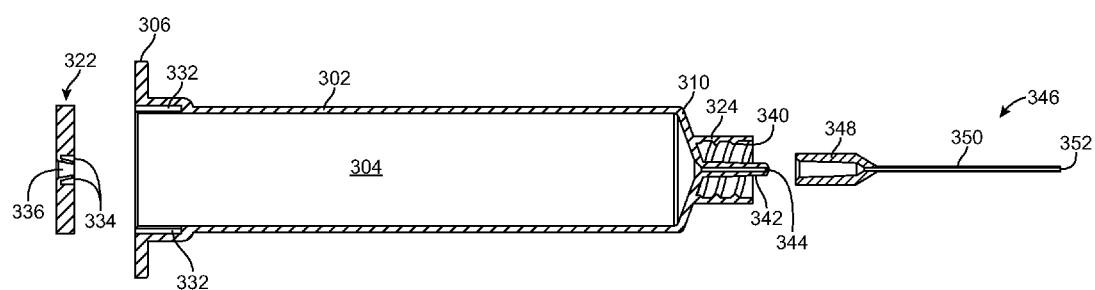
FIG. 46 illustrates barrel portions of the embodiment illustrated in FIG. 44, in an unassembled configuration.
Figure 47:
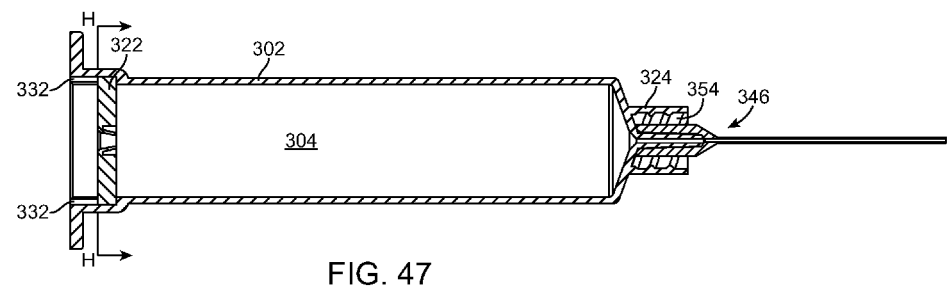
FIG. 47 illustrates the portions of FIG. 46 in an assembled configuration.

With reference to FIGS. 46 and 47, the barrel 302 is described in greater detail. A pair of slots 332 is formed on the interior surface at the proximal end of the barrel 302, extends distally a short distance, and each is sized to receive the stabilizer bar 322. The stabilizer bar 322 includes a through bore 336 in the center of the bar, and at least one, and preferably numerous resilient tangs 334 which are oriented distally and are angled towards the center of the bore 336. The collar 324 at the distal end of the barrel 302 is internally threaded with threads 340. A tapered conduit 342 is located at the distal and of the barrel 302 and includes a central lumen 344 which communicates with the interior 304 of the barrel. A cannula assembly 346, similar in structure to the cannula assemblies 10, 60, includes a proximal hub 348 and a cannula 350 mounted to the hub. The hub 348 is sized to fit over the exterior of the tapered conduit 342 and form a fluid sealed therewith, so that the lumen 344 will be in sealed fluid communication with the distal end 352 of the cannula 350. With reference to FIG. 47, in which the stabilizer bar 322 is positioned in the slots 332 and the cannula assembly 346 is mounted over the tapered conduit 342, it can be seen that an annular space 354 is formed between the exterior surface of the hub 348 and the threads 340. As with the previously described embodiment, and as described in greater detail below, annular space 354 is provided so that an additional needle-and-hub assembly can be mounted to the syringe and over the cannula assembly 346 for the purpose of aspirating fluid into the syringe barrel.

Figure 48:
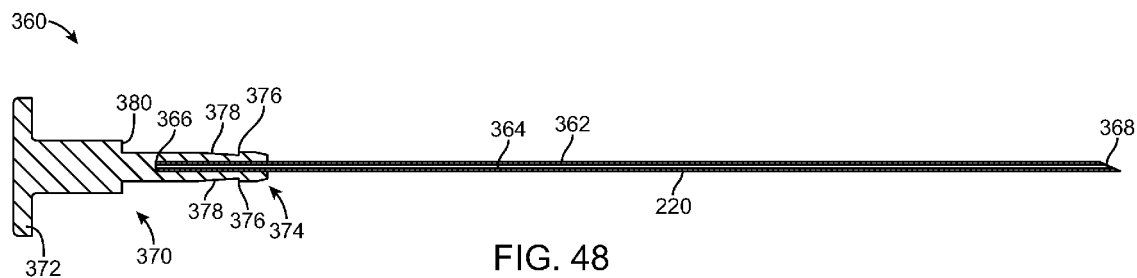
FIG. 48 illustrates a needle portion of the embodiment of FIG. 44.

FIG. 48 illustrates an exemplary embodiment of a blind needle 360 in accordance with principles of the present invention. The blind needle 360 includes a long needle shaft 362 having a lumen 364 extending between the proximal end 366 and a sharpened open distal end 368. A proximal body 370 is mounted to and seals the proximal end 366 of the needle shaft 362 and is provided and sized so that the digit of a practitioner can push against the proximal body and distally move the blind needle 360, as described in greater detail below. The proximal body 370 includes an enlarged proximal end 372 and a distal portion 374 in which the proximal and 366 of the needle shaft 362 is embedded. A shoulder 376, which is preferably circumferential, is formed near the distal end of the distal portion 374 and is formed in part by a tapered section 378 just proximal of the shoulder 376. While difficult to see in FIG. 48, holes 220 are formed through the side wall of the needle shaft 362 so that fluid which enters into the lumen 364 can flow distally out of the distal end 368 and proximally into the syringe barrel, as described elsewhere herein.

Figure 49:
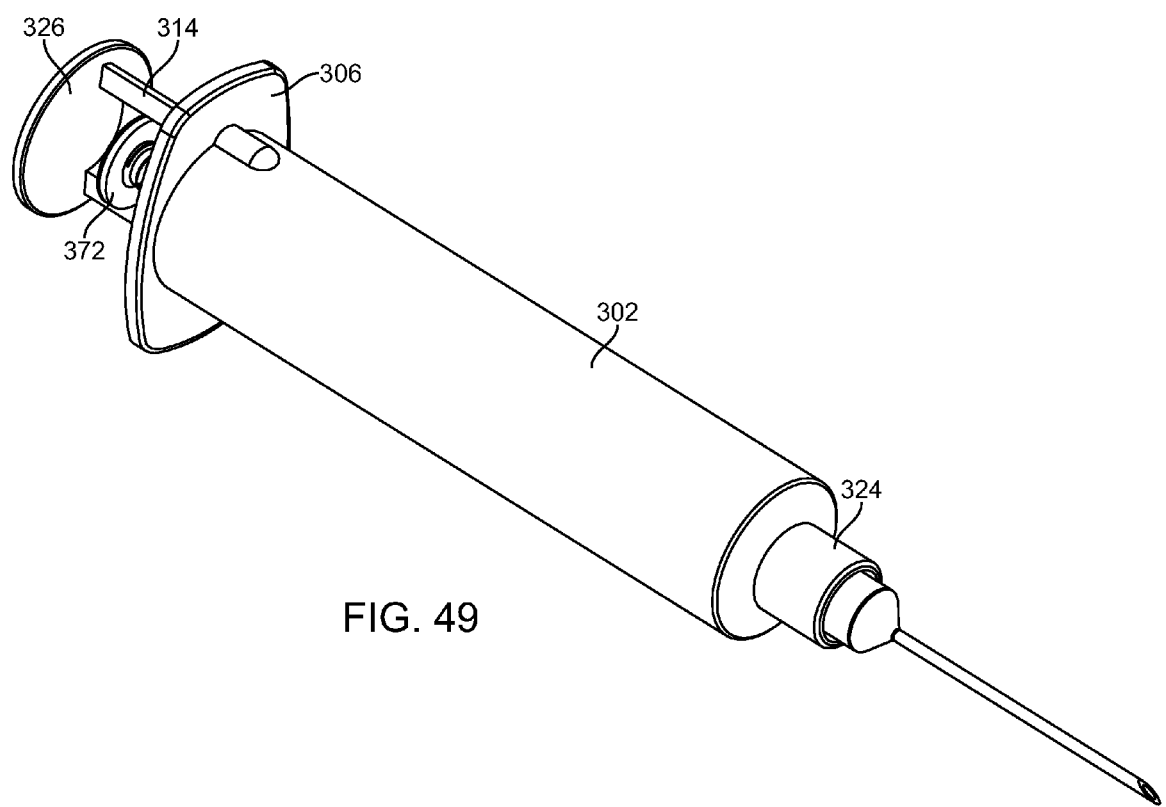
FIG. 49 illustrates a perspective view of the embodiment of FIG. 44.

FIG. 49 is a perspective illustration of the needle assembly 300, and better illustrates how the plunger stem 314 provides easy access for the practitioner to the large proximal end of 372 of the blind needle 360.

Figure 50:
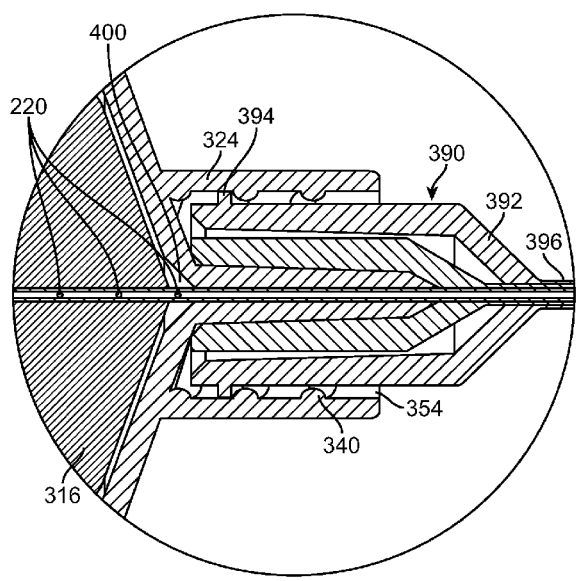
FIG. 50 illustrates an enlarged longitudinal cross-section view of the embodiment of FIG. 44, with the plunger in a distalmost position, and with an aspiration needle assembly.
Figure 51:
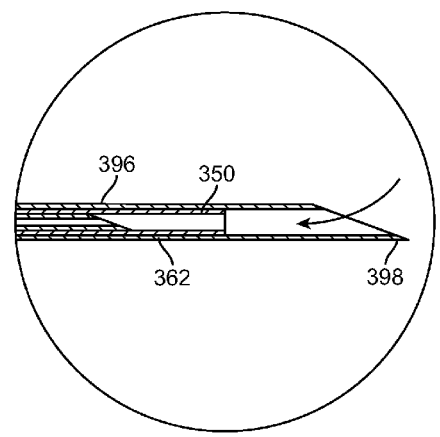
FIG. 51 illustrates the distalmost ends of a needle, cannula, and aspiration needle of the embodiment of FIG. 44.

FIGS. 50 and 51 are enlarged longitudinal cross-sectional illustrations of portions of the needle assembly 300. With reference to FIG. 50, the aspiration needle assembly 390 is illustrated in its position mounted within the annular space 354. The aspiration needle assembly 390 includes a hollow hub 392 which includes an external thread or bead 394 which is sized and configured to engage with the internal threads 340. The aspiration needle assembly 390 includes a distally extending hollow needle 396 which is sized to receive, within its lumen, the cannula 350.

The syringe barrel includes, at its distal-most interior portions, an enlarged space 400, which may be conical, frusto-conical, cylindrical, or any other desired shape. The enlarged space 400 is provided so that the holes 220 in the blind needle 362 are always in fluid communication with the interior of the syringe barrel 302. More specifically, as illustrated in FIG. 50, when the piston 316 is in its distal-most position, at least one of the holes 220 are located in the enlarged space 400, when the needle 362 is in any position between its most distally retracted position and its most proximally retracted position. With reference to FIG. 51, the distal end of the blinded needle 362 is illustrated in a proximal and retracted position relative to the needle 396 and the cannula 350. The sharpened distal end of the needle 398 can be used to pierce the septum of a medication vial and to aspirate the medication from the vial through the cannula 350, through the lumen of the blind needle 362, out the holes 220, and into the interior 304 of the syringe barrel 302.

Figure 52:
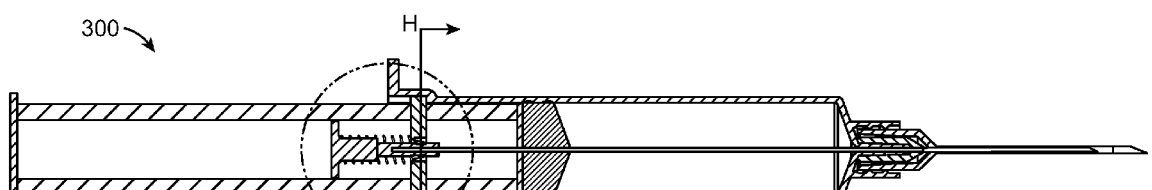
FIG. 52 illustrates a longitudinal cross-sectional view similar to that of FIG. 44.
Figure 53:
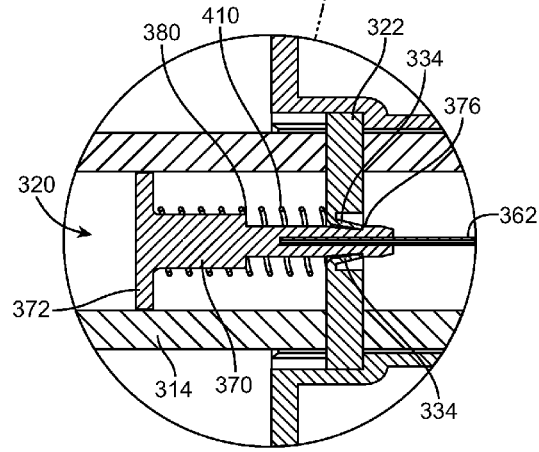
FIG. 53 illustrates an enlarged view of the encircled portion of FIG. 52.
Figure 54:
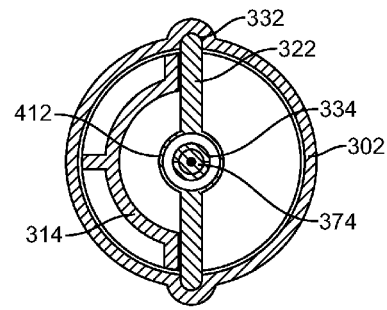
FIG. 54 illustrates a lateral cross-sectional view taken at line H-H in FIG. 52.

FIG. 52 illustrates a cross-sectional view of the needle assembly 300, while FIG. 53 illustrates an enlarged view of the proximal end of the syringe barrel, and FIG. 54 illustrates a lateral cross-sectional view taken at line H-H of FIG. 52. With reference to FIG. 53, the needle assembly 320 is illustrated in a proximal, retracted position. The proximal body 370 is mounted in the stabilizer bar 322, with the resilient tangs 334 are engaged against the shoulder 376. In this configuration, the enlarged proximal end 372 of the blind needle 360 bears against the stabilizer bar 322, and is urged proximally by a spring 410 which is mounted around the proximal body 370 and pushes against the distal face of the enlarged proximal end 372 and against the proximal face of the stabilizer bar 322. In this configuration, the distal end 368 of the blind needle 360 is positioned proximally of the distal end of the cannula 350. With reference to FIG. 54, the stabilizer bar 322 optionally includes a cylindrical collar 412 which is sized to form an annular space between the proximal body 370 and the collar, to receive and retain the spring 410. The longitudinal length of the collar 412 is selected to not interfere with the longitudinal movement of the needle assembly 320 with respect to the stabilizer bar 322.

Figure 55:
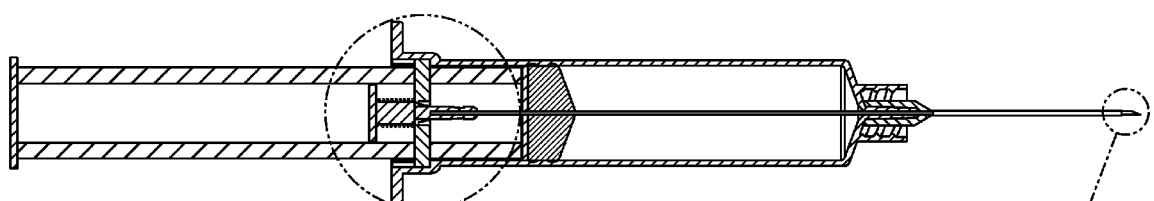
FIG. 55 illustrates a longitudinal cross-sectional view similar to that of FIG. 44, with the needle in a distalmost position.
Figure 56:
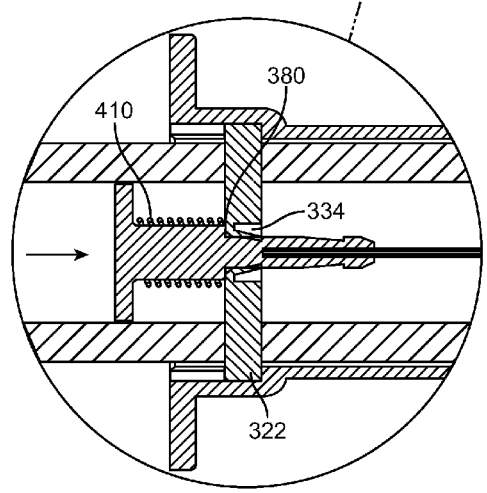
FIG. 56 illustrates an enlarged view of the encircled proximal portion of FIG. 55.
Figure 57:
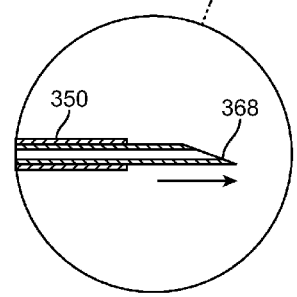
FIG. 57 illustrates an enlarged view of the encircled distal portion of FIG. 55.

FIG. 55 illustrates a longitudinal cross-sectional view similar to that of FIG. of 52, but with the needle assembly 320 in a distal position; FIG. 56, like FIG. 53, illustrates an enlarged view of the proximal end of the syringe barrel, while FIG. 57 illustrates an enlarged view of the distal and of the cannula and needle. As can be seen in FIG. 56, when the practitioner has pushed the needle assembly 320 in a distal direction, e.g., by pressing on the enlarged proximal end 372, the spring 410 is compressed and the resilient tangs 334 of the stabilizer bar are spread radially and ride along the outside of the tapered section 378 of the proximal body 370, until the shoulder 380 engages against the proximal face of the bar 322. This distal motion of the needle assembly 320 advances the needle tip 368 outside and distal of the distal end of the cannula 350, so that the assembly can be used to penetrate tissue, as described elsewhere herein. Preferably, before the practitioner pushes on the proximal portion of the needle assembly 320, the aspiration needle assembly, described with reference to FIGS. 50 and 51, has been removed, exposing the exterior surface of the cannula 350.

Figure 58:
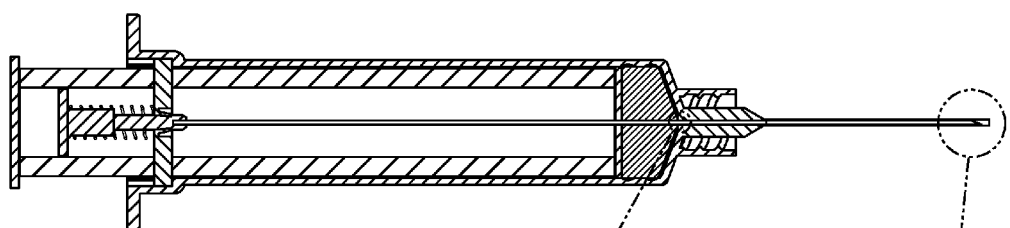
FIG. 58 illustrates a longitudinal cross-sectional view similar to that of FIG. 44, with the needle in a proximalmost position and the plunger in a distalmost position.
Figure 59:
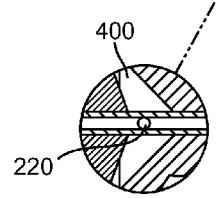
FIG. 59 illustrates an enlarged view of the encircled proximal portion of FIG. 58.
Figure 60:
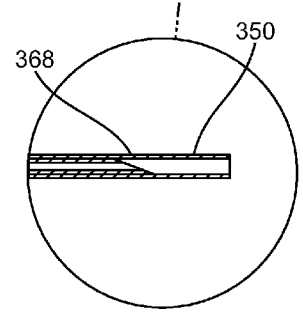
FIG. 60 illustrates an enlarged view of the encircled distal portion of FIG. 58.

With reference to FIGS. 58 through 60, the practitioner can now release their digit from the needle assembly 320, permitting the spring 410 to urge the needle assembly 320 in the proximal direction, causing the sharpened distal tip 368 of the needle to retract proximally within the cannula 350. The practitioner can then push distally on the plunger flange 326, causing the piston 316 to move distally within the syringe barrel 302, expelling the contents of the syringe through the holes 220 into the lumen of the needle, out the distal end of the needle in the cannula, and in 2 the anatomical space of interest. As again illustrated in FIG. 59, the enlarged space 400 helps ensure that fluid can enter into the holes 220 along the length of the needle when the needle is in any proximal or distal position.

According to exemplary embodiments of the present embodiment described above with reference to FIG. 44 et sqq., the sheath stops at the distal end of the syringe barrel at its hub. In accordance with yet another exemplary embodiment, the sheath extends proximally through its hub most of the distance into the proximal end of the syringe barrel, and includes holes which align with holes 220. Extending the sheath proximally into the barrel assists in preventing the plunger from pushing the needle out the end of the sheath when the plunger is pushed to inject the anesthetic. The sheath advantageously does not extend proximally all the way to the proximal end of the syringe, but instead leaves a gap between the proximal end of the sheath and the distal end of the proximal body 370. This gap allows room for the needle assembly to be pushed into the syringe barrel.

Figure 61:
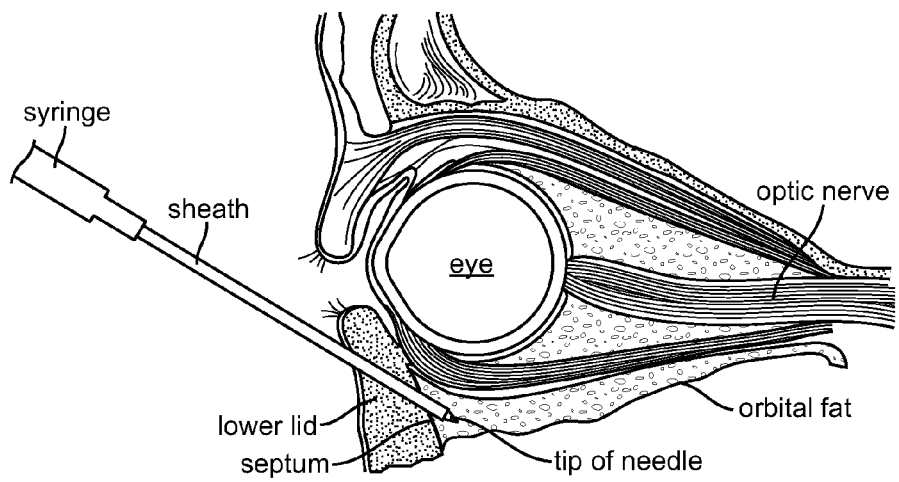
FIG. 61 illustrates a vertical cross-sectional view of the anatomy of the human orbit and adjacent structures, during a first stage of a retrobulbar injection according to yet another exemplary embodiment of the invention.
Figure 62:
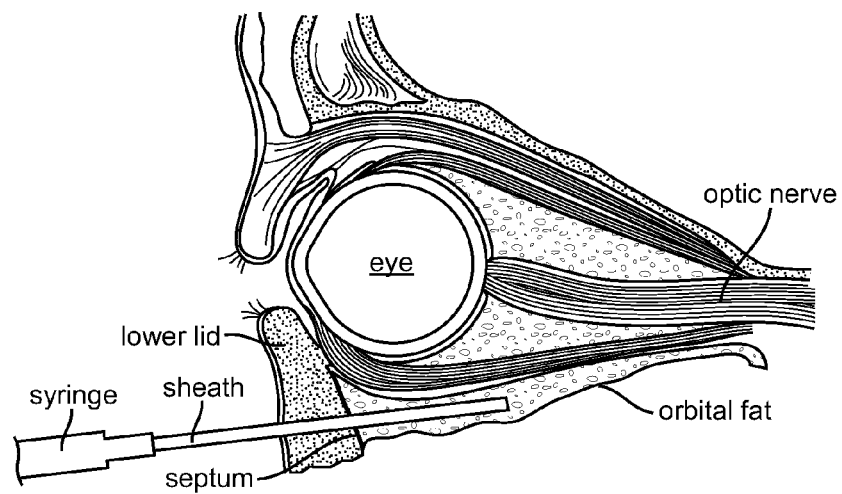
FIG. 62 illustrates a vertical cross-sectional view of the anatomy of the human orbit and adjacent structures, during a second stage of the embodiment of a retrobulbar injection of FIG. 61.

FIGS. 61 and 62 illustrate another exemplary method embodying principles of the present invention. A retrobulbar needle assembly, which is advantageously constructed in accordance with principles of the present invention, with the needle tip exposed, is pushed through the lateral lower lid skin, muscle, and orbital septum and into the orbit. During this step, the needle tip is directed towards the orbital floor, and is thus not directed toward the globe. With reference to FIG. 62, after the needle tip has penetrated the lower lid skin, muscle, and orbital septum, the practitioner manipulates the needle assembly, such as by releasing the button 204 or retracting the inner hub holder 54 proximally when using embodiments described herein, to retract the needle tip proximally and into the overlying sheath. The needle assembly, including the needle and sheath, is then reoriented horizontally or superiorly relative to the globe, and the sheath is pushed further into the orbit, including the orbital fat. Once the distal tip of the sheath has been advanced to the desired location, the practitioner can inject the contents of the syringe, e.g., an anesthetic, into the patient.

Figure 63:
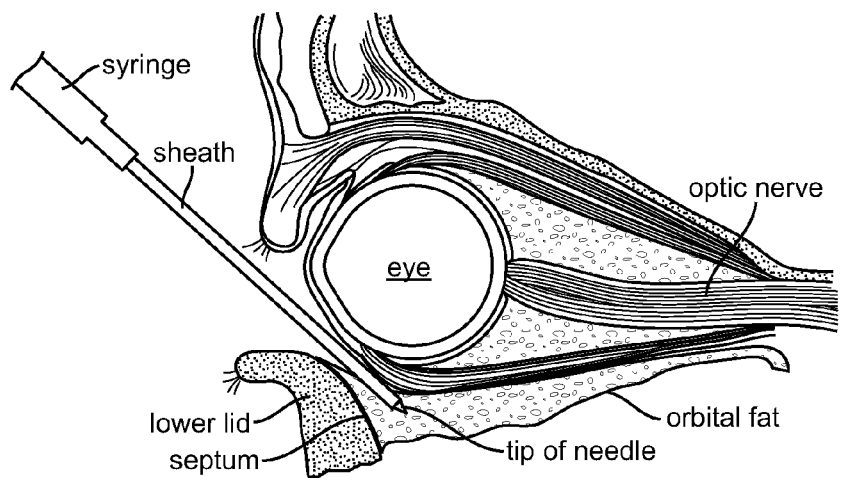
FIG. 63 illustrates a vertical cross-sectional view of the anatomy of the human orbit and adjacent structures, during a first stage of a retrobulbar injection according to further exemplary embodiment of the invention.
Figure 64:
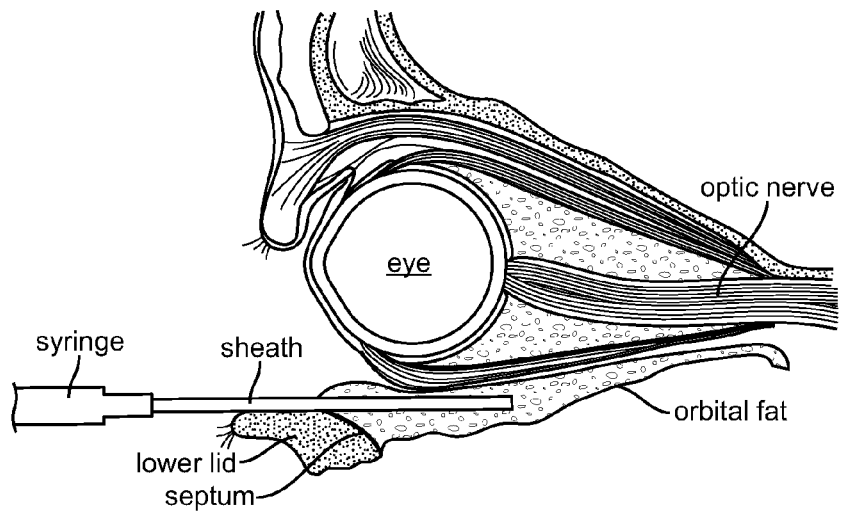
FIG. 64 illustrates a vertical cross-sectional view of the anatomy of the human orbit and adjacent structures, during a second stage of the further embodiment of a retrobulbar injection of FIG. 63.

FIGS. 63 and 64 illustrate another exemplary method embodying principles of the present invention. The patient's lower lid is everted by the practitioner, and a retrobulbar needle assembly, which is advantageously constructed in accordance with principles of the present invention, with the needle tip exposed, is pushed inferiorly through the conjunctiva to avoid the globe, and into the orbit. As with the exemplary embodiment described above with reference to FIGS. 61 and 62, the practitioner manipulates the needle assembly, such as by releasing the button 204 or retracting the inner hub holder 54 proximally when using embodiments described herein, to retract the needle tip proximally and into the overlying sheath. The needle assembly, including the needle and sheath, is then reoriented horizontally or superiorly relative to the globe, and the sheath is pushed further into the orbit, including the orbital fat. Once the distal tip of the sheath has been advanced to the desired location, the practitioner can inject the contents of the syringe, e.g., an anesthetic, into the patient.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

I claim:

1. A syringe comprising:
    a cylindrical barrel having a proximal end, a distal end, an interior wall, and an open interior space between the proximal and distal ends;
    a plunger assembly including
        a plunger stem having a proximal end and a distal end, and
        a piston attached to the plunger stem distal end, the piston forming a fluid seal with the barrel interior wall;
    a cannula including
        a proximal hub attached to the barrel distal end, the hub having a hollow interior,
        a proximal portion attached to the hub,
        a distal portion having a flexibility greater than the cannula proximal portion, and
        a lumen extending longitudinally between the proximal portion and the distal portion and in fluid communication with the hub hollow interior; and
    a needle assembly including
        a longitudinally extending shaft having a proximal end, a distal end, and a lumen extending proximally from the needle shaft distal end,
        at least one side hole formed along the needle shaft, and
        a proximal body mounted to the needle shaft proximal end, the proximal body sealing the proximal end of the needle shaft lumen, the proximal body positioned proximal of the piston;
    wherein the needle assembly is longitudinally movable relative to the barrel and the cannula between a distal position at which the needle shaft distal end is distal of the cannula distal end, and a proximal position at which the needle shaft distal end is proximal of the cannula distal end; and
    wherein the needle shaft distal end is positioned within the cannula proximal portion when in the proximal position.

2. The syringe according to claim 1, wherein the at least one side hole in the needle shaft is located along the needle shaft so that the at least one side hole is in fluid communication with the barrel interior space when the needle assembly is at any position between the distal position and the proximal position.

3. The syringe according to claim 1, wherein the proximal body is positioned between the plunger stem proximal and distal ends.

4. The syringe according to claim 1, wherein the plunger stem has a laterally open space between the plunger stem proximal and distal ends.

5. The syringe according to claim 1, wherein the plunger stem is positioned laterally offset from the needle assembly proximal body.

6. The syringe according to claim 1, wherein the needle assembly shaft extends through the piston and through the cannula proximal portion.

7. The syringe according to claim 1, further comprising: a cavity formed on the distal end of the barrel interior wall, the needle assembly shaft extending through the cavity.

8. The syringe according to claim 1, wherein the cannula includes a proximal end positioned within the barrel interior.

9. A syringe comprising:
a cylindrical barrel having a proximal end, a distal end, an interior wall, and an open interior space between the proximal and distal ends;
a plunger assembly including
a plunger stem having a proximal end and a distal end, and
a piston attached to the plunger stem distal end, the piston forming a fluid seal with the barrel interior wall;
a cannula including
a proximal hub attached to the barrel distal end, the hub having a hollow interior,
a proximal portion attached to the hub,
a distal portion having a flexibility greater than the cannula proximal portion, and
a lumen extending longitudinally between the proximal portion and the distal portion and in fluid communication with the hub hollow interior; and
a needle assembly including
a longitudinally extending shaft having a proximal end, a distal end, and a lumen extending proximally from the needle shaft distal end,
at least one side hole formed along the needle shaft, and
a proximal body mounted to the needle shaft proximal end, the proximal body sealing the proximal end of the needle shaft lumen, the proximal body positioned proximal of the piston;
a stabilizer bar mounted laterally across the barrel, the stabilizer bar including a longitudinally extending bore, a portion of the needle assembly extending through the stabilizer bar bore; and
a spring extending between the needle assembly proximal body and the stabilizer bar, the spring biasing the needle assembly in a proximal direction.

10. A syringe comprising:
a cylindrical barrel having a proximal end, a distal end, an interior wall, and an open interior space between the proximal and distal ends;
a plunger assembly including
a plunger stem having a proximal end and a distal end, and
a piston attached to the plunger stem distal end, the piston forming a fluid seal with the barrel interior wall;
a cannula including
a proximal hub attached to the barrel distal end, the hub having a hollow interior,
a proximal portion attached to the hub,
a distal portion having a flexibility greater than the cannula proximal portion, and
a lumen extending longitudinally between the proximal portion and the distal portion and in fluid communication with the hub hollow interior; and
a needle assembly including
a longitudinally extending shaft having a proximal end, a distal end, and a lumen extending proximally from the needle shaft distal end,
at least one side hole formed along the needle shaft, and
a proximal body mounted to the needle shaft proximal end, the proximal body sealing the proximal end of the needle shaft lumen, the proximal body positioned proximal of the piston; and
a stabilizer bar mounted laterally across the barrel, the stabilizer bar including a longitudinally extending bore, a portion of the needle assembly extending through the stabilizer bar bore;
wherein the stabilizer bar includes at least one tang in the stabilizer bar bore oriented partially distally;
wherein the proximal body includes a distal shoulder oriented proximally; and
wherein the tang engages against the distal shoulder.

11. A syringe comprising:
a cylindrical barrel having a proximal end, a distal end, an interior wall, and an open interior space between the proximal and distal ends;
a plunger assembly including
a plunger stem having a proximal end and a distal end, and
a piston attached to the plunger stem distal end, the piston forming a fluid seal with the barrel interior wall;
a cannula including
a proximal hub attached to the barrel distal end, the hub having a hollow interior,
a proximal portion attached to the hub,
a distal portion having a flexibility greater than the cannula proximal portion, and
a lumen extending longitudinally between the proximal portion and the distal portion and in fluid communication with the hub hollow interior; and
a needle assembly including
a longitudinally extending shaft having a proximal end, a distal end, and a lumen extending proximally from the needle shaft distal end,
at least one side hole formed along the needle shaft, and
a proximal body mounted to the needle shaft proximal end, the proximal body sealing the proximal end of the needle shaft lumen, the proximal body positioned proximal of the piston; and
a stabilizer bar mounted laterally across the barrel, the stabilizer bar including a longitudinally extending bore, a portion of the needle assembly extending through the stabilizer bar bore;
wherein the needle assembly proximal body includes a proximal shoulder having a lateral size greater than a lateral size of the stabilizer body bore.

* * * * *